United States Patent [19]

Hunter

[11] Patent Number: 5,466,445

[45] Date of Patent: * Nov. 14, 1995

[54] METHODS FOR REDUCING SALMONELLA IN CHICKENS

[75] Inventor: Robert L. Hunter, Tucker, Ga.

[73] Assignee: Emory University, Atlanta, Ga.

[ * ] Notice: The portion of the term of this patent subsequent to Feb. 2, 2010, has been disclaimed.

[21] Appl. No.: 74,069

[22] Filed: Jul. 21, 1993

Related U.S. Application Data

[63] Continuation-in-part of Ser. No. 714,258, Jun. 12, 1991, Pat. No. 5,234,683, which is a continuation of Ser. No. 107,358, Oct. 9, 1987, Pat. No. 5,114,708, which is a continuation-in-part of Ser. No. 90,795, Aug. 28, 1987, abandoned, which is a continuation-in-part of Ser. No. 872,111, Jun. 13, 1986, abandoned, which is a continuation-in-part of Ser. No. 787,770, Oct. 15, 1985, abandoned, which is a continuation-in-part of Ser. No. 745,917, Jun. 18, 1985, abandoned.

[51] Int. Cl.$^6$ .................. A61K 31/74; A61K 31/075
[52] U.S. Cl. .................. 424/78.31; 514/716
[58] Field of Search .................. 424/78.31; 514/716

[56] References Cited

U.S. PATENT DOCUMENTS

| | | | |
|---|---|---|---|
| 2,861,887 | 11/1958 | Colby et al. | 514/723 |
| 2,979,528 | 4/1961 | Lundsted | 564/505 |
| 3,740,421 | 6/1973 | Schmolka | 424/65 |
| 3,849,550 | 11/1974 | Teitelbaum et al. | 424/78.29 |
| 3,932,659 | 1/1976 | Green et al. | 514/668 |
| 4,073,886 | 2/1978 | Kohn | 530/383 |
| 4,309,413 | 1/1982 | Fields et al. | 424/78.21 |
| 4,407,790 | 10/1983 | Oakes | 514/723 |
| 4,510,146 | 4/1985 | Lechtken et al. | 514/312 |
| 4,557,898 | 12/1985 | Green et al. | 422/28 |
| 5,183,687 | 2/1993 | Hunter et al. | 424/78.34 |
| 5,234,683 | 8/1993 | Hunter et al. | 424/78.31 |

FOREIGN PATENT DOCUMENTS

PCT/US86/01315  6/1986  WIPO .

OTHER PUBLICATIONS

Amiji, M. et al., "Prevention of Protein adsorption and platelet adhesion on surfaces by PEO/PPO/PEO triblock copolymers," *Biomaterials*, vol. 13, No. 10, pp. 682–692 (1992).

Schmolka, "A Review of Block Polymer Surfactants," *Journal of American Oil Chemists Society*, vol., 54, No. 3, pp. 110–116 (1977).

Hunter and Bennett, "The Adjuvant Activity of Nonionic Block Polymer Surfactants," *Journal of Immunology*, vol. 133, pp. 3167–3175 (1984).

Hunter et al., "The Adjuvant Activity of Nonionic Block Polymer Surfactants," *Journal of Immunology*, vol. 127, pp. 1244–1250 (1981).

Atkinson et al., "Induction of Suppressor Cells by Reverse Block Copolymers," Abstract #7596, *Federation Proceedings*, vol. 44, p. 1710 (Mar. 1985).

Kendall, "Have We Underestimated the Importance of the Thymus in Man?" *Experentia*, vol. 40, pp. 1181–1185 (1982).

Hunter et al., "The Adjuvant Activity of Nonionic Block Polymer Surfactants," *Scand. Journal of Immunology*, vol. 23, pp. 287–300 (1986).

Hunter et al., *Advances in Carriers & Adjuvant for Veterinary Biologics*, The Iowa State University Press, "Structural Basis of the Activity of the Surface–Active Adjuvants", Chapter 6, pp. 61–70 (1986).

Ceresa, Editor, "The Applications of Block Polyol Surfactants," *Block and Graft Copolymerization*, vol. 2, pp. 174–272 (1976).

*Primary Examiner*—Raymond Henley, III
*Assistant Examiner*—K Weddington
*Attorney, Agent, or Firm*—Jones & Askew

[57] ABSTRACT

A new class of biologically-active copolymers is provided capable of effecting biological systems in many different ways. The biologically active copolymers of the present invention also have a wide variety of effects on individual cells. The biologically active copolymers are also effective against certain microorganisms. The biologically active copolymers of the present invention can be administered to animals to provide specific effects on certain microorganisms that reside in the gut of the animal. A preferred use is administering the biologically active copolymers of the present invention to poultry to reduce the number of Salmonella in the poultry gut.

25 Claims, 6 Drawing Sheets

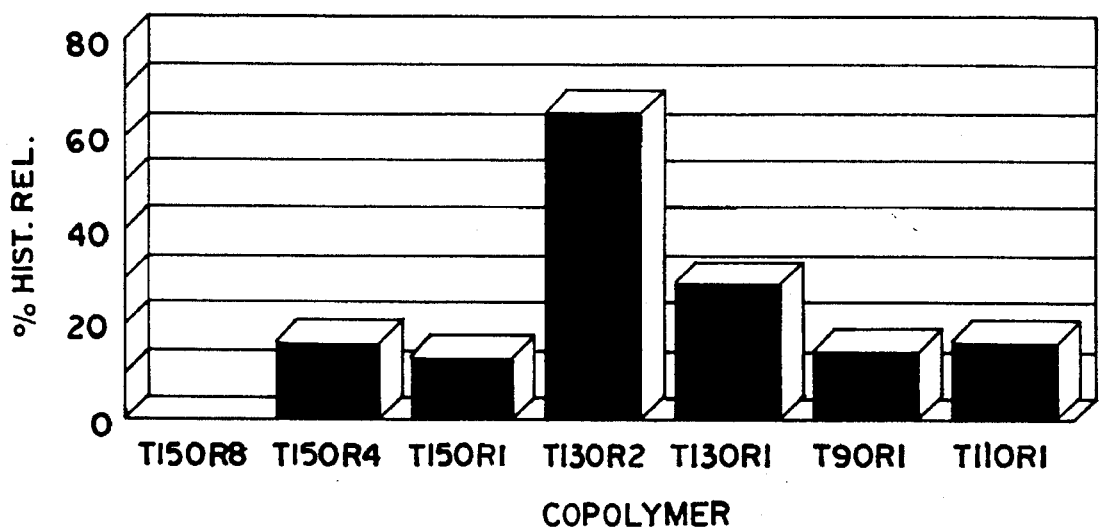
Fig_1
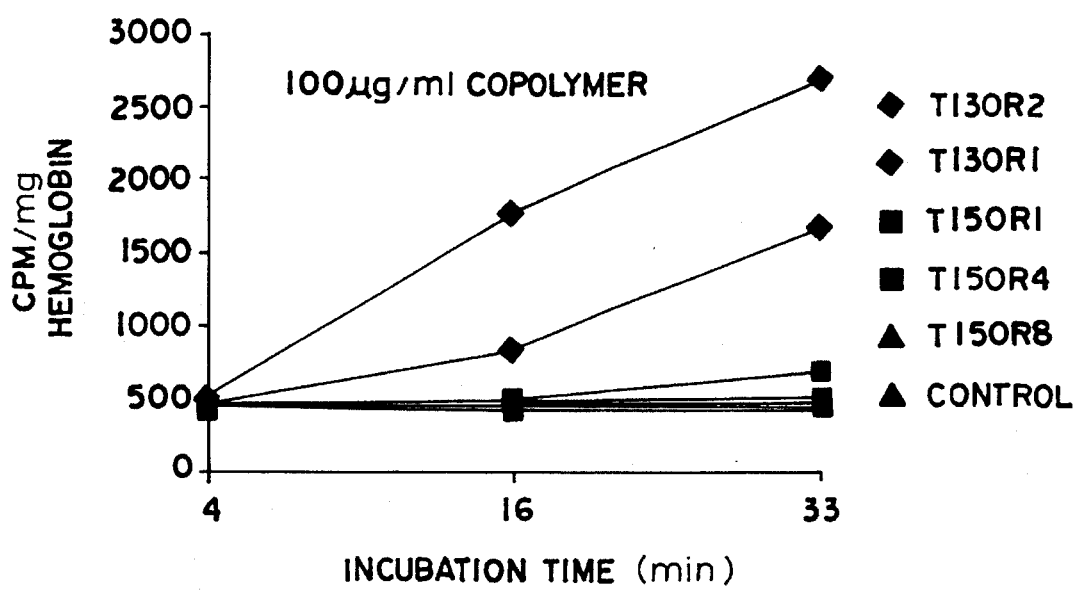
Fig_2

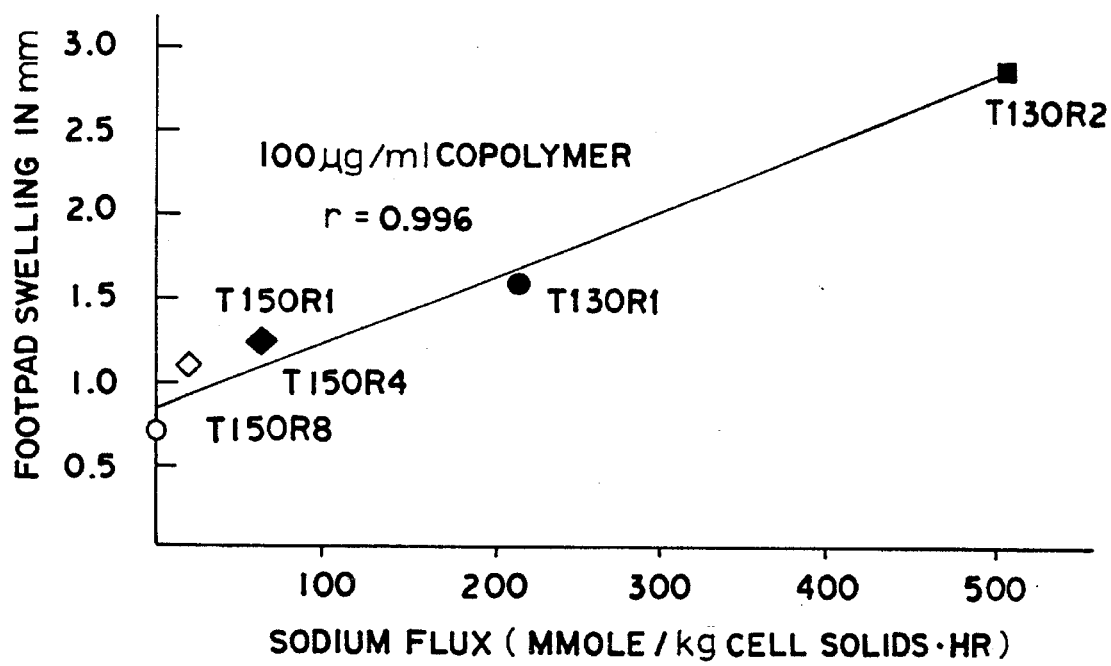
Fig_3
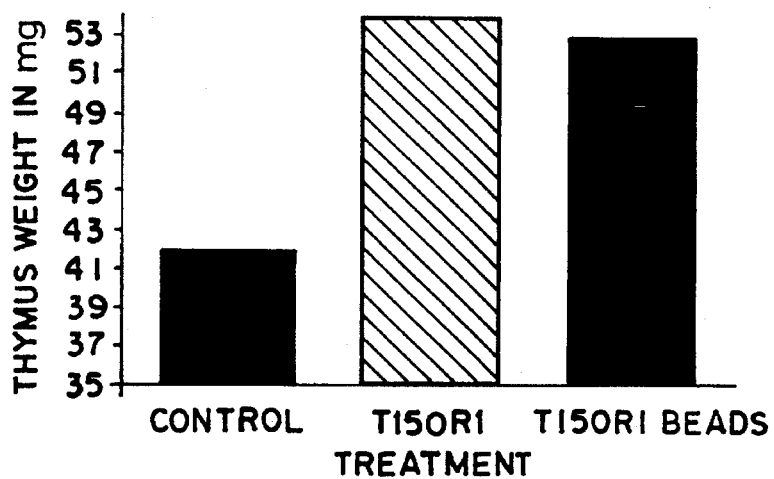
Fig_4

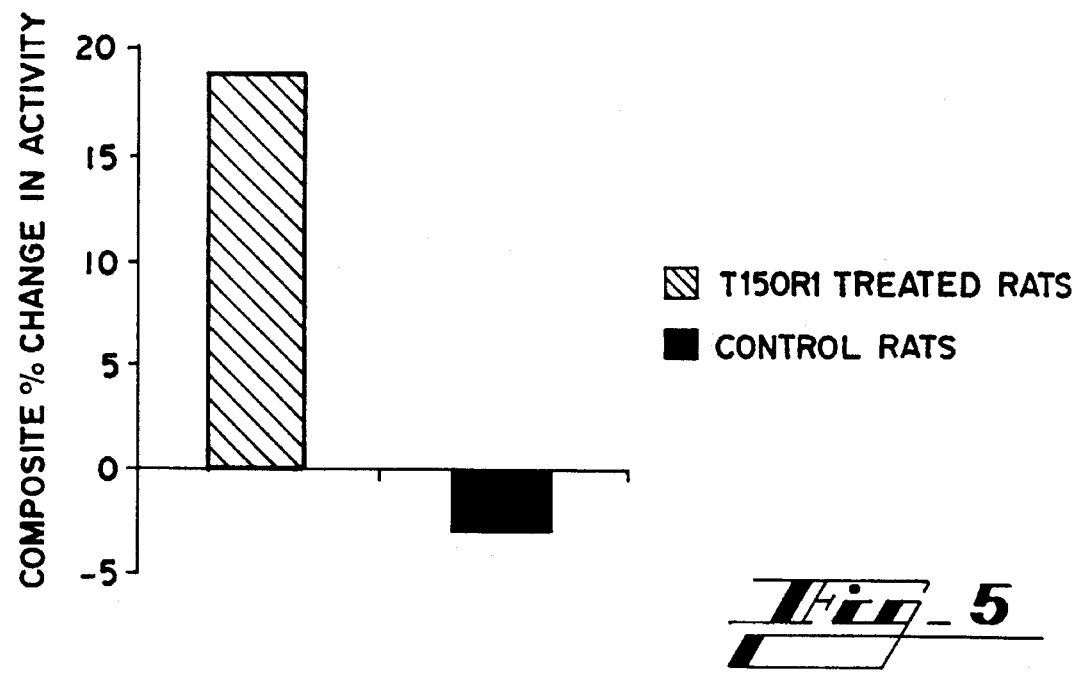
Fig_5
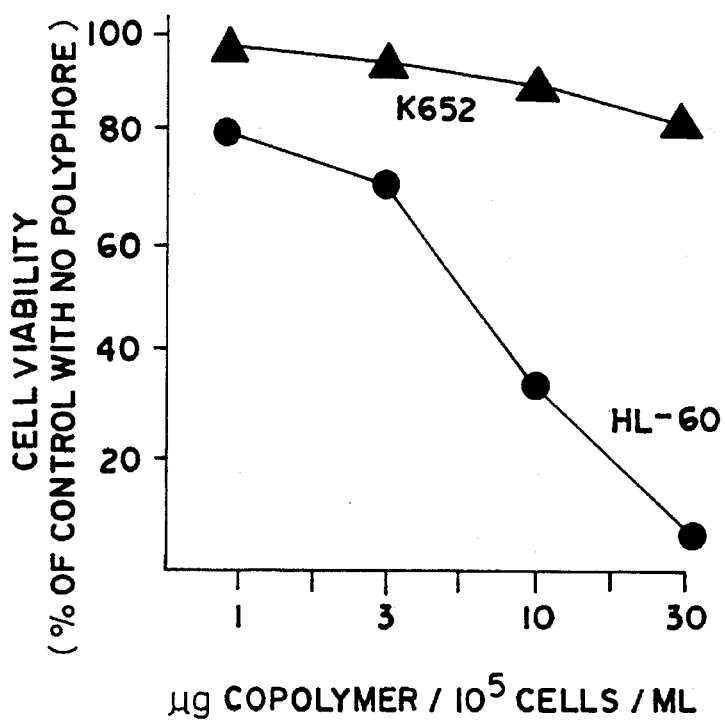
Fig_6

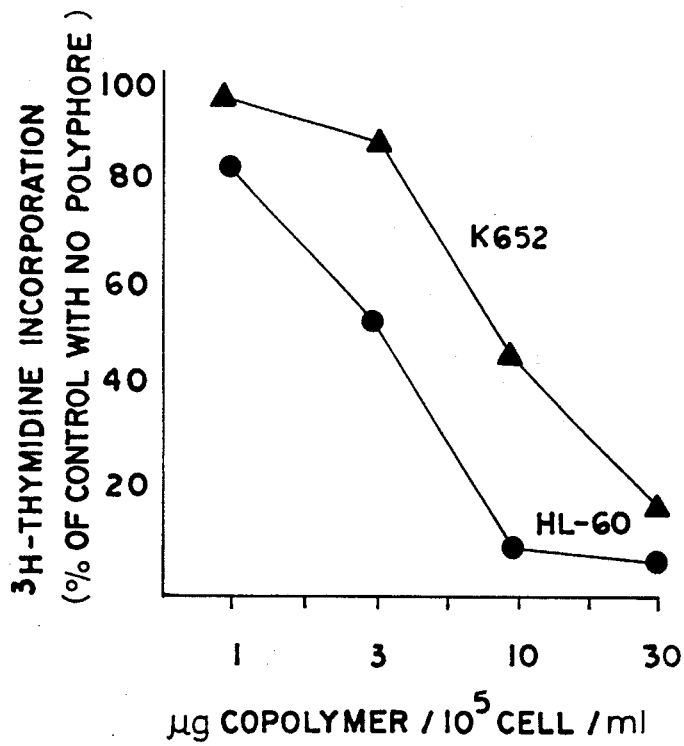
Fig_7
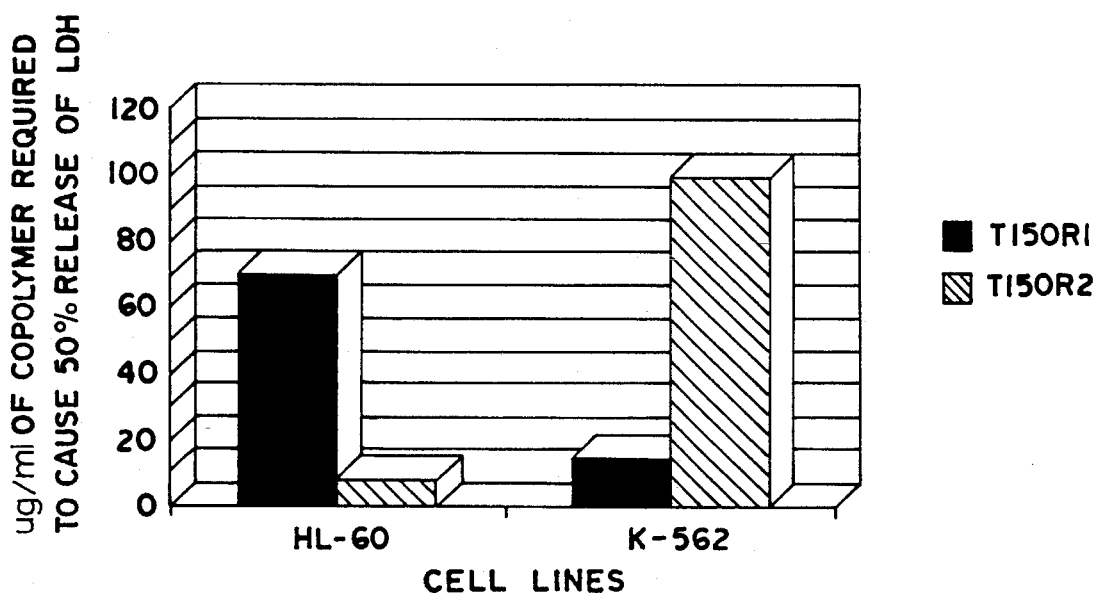
Fig_8

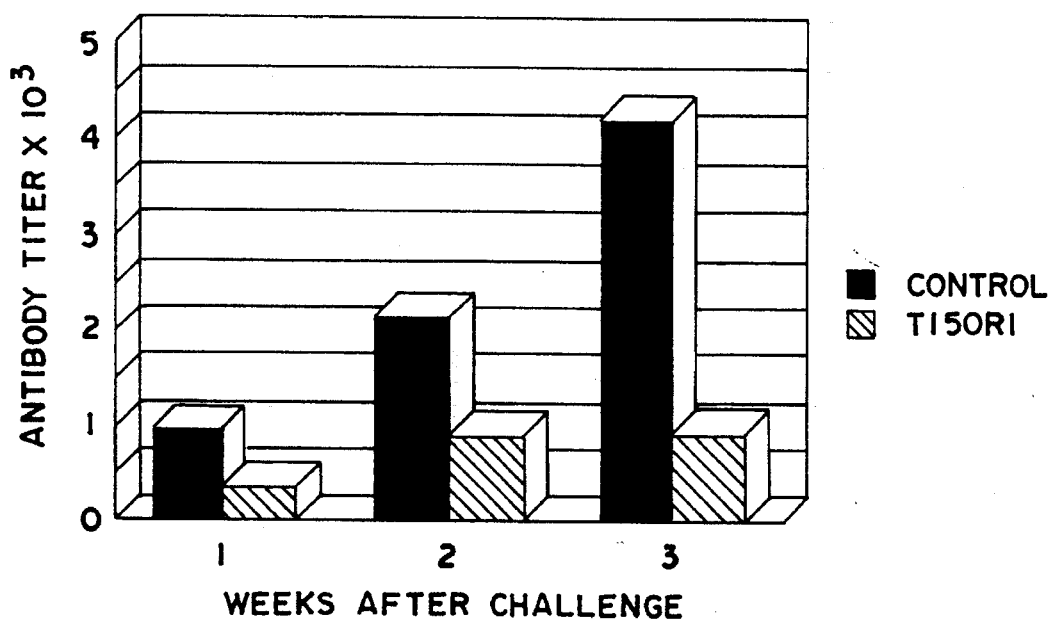
Fig_9
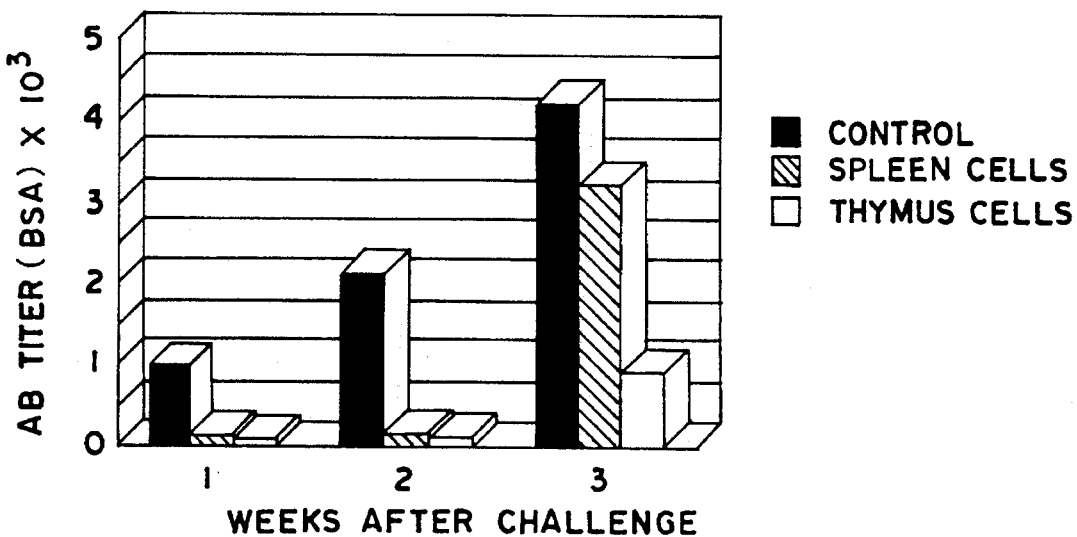
Fig_10

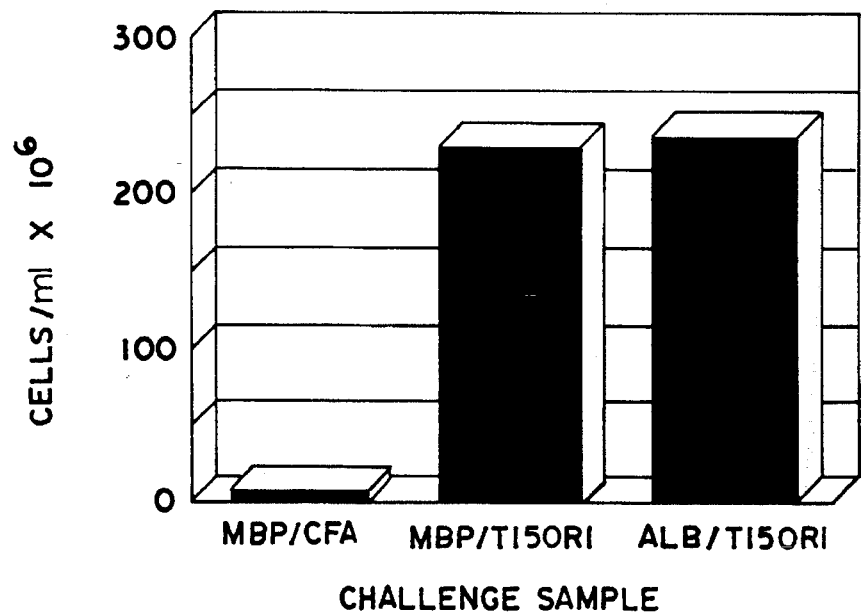
*Fig_11*
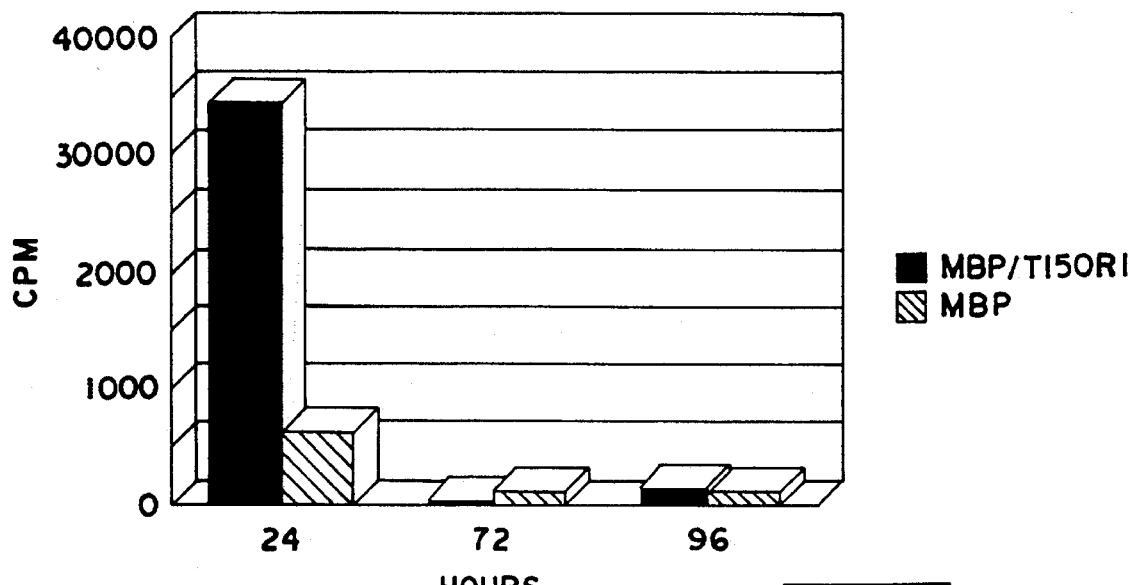
*Fig_12*

METHODS FOR REDUCING SALMONELLA IN CHICKENS

CROSS-REFERENCE TO RELATED APPLICATIONS

This application is a continuation-in-part of U.S. application Ser. No. 07/714,258, filed Jun. 12, 1991, now U.S. Pat. No. 5,234,683, which is a continuation of U.S. application Ser. No. 07/107,358, filed Oct. 9, 1987, now U.S. Pat. No. 5,114,708, which is a continuation-in-part of U.S. application Ser. No. 07/090,795, filed Aug. 28, 1987, now abandoned, which is a continuation-in-part of U.S. application Ser. No. 06/872,111, filed Jun. 13, 1986, now abandoned, which is a continuation-in-part of U.S. application Ser. No. 06/787,770, filed Oct. 15, 1985, now abandoned, which is a continuation-in-part of U.S. application Ser. No. 06/745,917, filed on Jun. 18, 1985, now abandoned.

TECHNICAL FIELD

The present invention relates to compounds with a variety of biological activities and more particularly, to a series of block copolymers that have a wide variety of effects on living cells and organisms.

BACKGROUND OF THE INVENTION

The present invention is a class of compounds that has a wide variety of profound biological effects. Background material concerning several of these biological activities is discussed hereinbelow.

IMMUNE STIMULATING COMPOUNDS

The immune system is a highly complex system of cells and tissues that requires the cooperation of a large number of different cell types. The systems of the body that make up the immune system network are variously categorized as belonging to the hematopoietic system, the reticuloendothelial or phagocytic system and the lymphoid system.

The hematopoietic system is located in the bone marrow and is responsible for supplying the various precursor and accessory cells of the immune systems. The reticuloendothelial system is made up of the phagocytic cells that are responsible for destroying or neutralizing foreign material that may enter the body. The lymphoid system is made up of lymphocytes, and is responsible for the overall regulation of the immune system and for the production of antibodies.

The tissues of the lymphoid system are generally classified as the central tissues and the peripheral tissues. Two central lymphoid tissues of mammals are bone marrow and thymus. In addition, fowl have a third central lymphoid organ, the bursa of Fabricius, which is critical to the development of the immunoglobulin-producing cells. It is thought that the mammals have a bursal equivalent associated with the intestinal tract. Lymph nodes, spleen, tonsils, intestinal lymphoid tissue (Peyer's patches) and other collections of lymphocytes constitute the peripheral lymphoid tissues.

In mammals, the bone marrow, if considered as a single tissue, is the largest tissue of the body. In the average human adult the total weight of the bone marrow is about 3 kg. Marrow fills the central core of nearly all bones. Bone marrow has three types of tissue; vascular tissue, adipose tissue and the tissue directed to hematopoiesis or blood cell formation. The vascular tissue is the circulatory system that supplies nutrients and removes wastes from the actively growing cells. The hematopoietic tissue is responsible for the formation of erythrocytes, platelets, granulocytes and monocytes, and lymphocyte precursors. Adipose tissue consists of fat cells which contribute little to the function of the bone marrow.

The other central lymphoid tissue is the thymus; a bilobed organ situated in the anterior thoracic cage over the heart. In other species, the thymus may be distributed along the neck and thorax in several lobules.

Embryologically, the thymus emerges from the third and fourth branchial pouches. The human thymus is a fully developed organ at birth and weighs 15 to 20 grams. By puberty it weighs 40 grams, after which it atrophies or involutes becoming less significant structurally and functionally. Atrophy of the thymus with age is a characteristic of all species which is associated with aging and the cessation of growth. The incidence of age related diseases increases as the thymus shrinks and thymus-dependent immunity decreases. This age-associated decrease in thymic weight, called involution, is accompanied by changes in the thymic structure and a general decline in thymic function. Transient involution of the thymus may also occur as a consequence of a stress or infection. Thymic involution may be controlled hormonally; castration slows involution while injection of corticosteroid hormones accelerates involution. Numerous studies have demonstrated that the thymic involution associated with increasing age parallels a reduction of T-lymphocyte-mediated immunity and increased incidence of diseases associated with aging. Many diseases and treatments can accelerate involution of the thymus; virtually none are known to enhance growth of the thymus or reverse involution.

Anatomically, the thymus is a pouch of epithelial cells filled with lymphocytes, nourished and drained by the vascular and lymphatic systems and innervated by the autonomic nerves. The epithelial cells and other structural cells divide the thymus into a complex assembly of continuous lobes, each of which is heavily laden with lymphocytes. The epithelial cells produce hormones and regulate some of the activities of the lymphocytes. The lymphocyte population is greatest in the cortex or outer portion of each lobule. The inner section, the medulla, has more epithelial cells and fewer lymphocytes but the lymphocytes are more mature.

Lymphocytes can generally be classified as either T-lymphocytes or as B-lymphocytes. B-lymphocytes are responsible for the production of antibodies (immunoglobulin) in response to a challenge by a particular antigen. T-lymphocytes are responsible for the general regulation of the immune system and are also the principal mediators in cell-mediated immune responses. They also influence the proliferation of bone marrow cells and are probably involved in the growth and differentiation of other organs as well.

All lymphocytes are ultimately derived from stem cells in bone marrow. These lymphocyte precursors are dispersed into the blood where they course through many organs. However, critical events take place in the thymus and bursa of Fabricius (or its mammalian equivalent) that imprint the lymphocytes with special functions and that regulate the development into either T or B-lymphocytes.

Life-span studies of lymphocytes of most mammalian species divide lymphocytes into two fractions—those with a short span (mostly large lymphocytes) of 5 to 7 days and the small lymphocytes with a life span measured in months or even years. The former are usually B-lymphocytes and the latter are usually T-lymphocytes.

B-lymphocytes respond to immunologic phenomena very differently from a T-lymphocyte in practically every instance. T-lymphocytes are formed in the thymus from lymphoblasts that left the bone marrow. This maturation is expressed morphologically as a reduction in cell size to about 7 µm in diameter. The thymic cortex is rich in lymphocytes of all sizes. These thymocytes are not morphologically distinguishable from lymphocytes in other tissues, but they are immature and antigenically identifiable by the presence of several cell surface antigens including the φ, or T antigen, a distinctive surface marker antigen that separates the T-lymphocyte from the B-lymphocyte.

Enumeration of lymphocytes indicate that 65% to 85% of all lymphocytes in the blood are of the T type. Lymphocytes of the thoracic duct fluid are nearly 90% to 95% of the T variety and those in the Peyer's patches or the gut are 50% to 65% T-lymphocytes. The T-lymphocyte population of lymph nodes, particularly in the deep cortical region, is high, but is low in the tonsil and the appendix.

When the T-lymphocyte contacts a recognizable antigen in the appropriate context, it passes through a phase of growth and cell division known as lymphocyte transformation to produce a large population of its own kind. The antigen must first be "processed" by macrophages and then presented to T-lymphocytes.

T-lymphocytes are actually divided into several subsets and the role that they play in the immune system is complex. The T-lymphocyte is responsible for the phenomenon known as the cell-mediated immune response. In a cell-mediated immune response, the T lymphocytes that recognize a cell-bound antigen begin producing and secreting a wide variety of proteins that affect the activity of other types of cells in the immune system. These proteins include lymphokines that attract, activate and hold phagocytes at the site of the antigen and interferons that provide protection against virus infection.

The T-lymphocyte is also an important regulator of B-lymphocyte function. The antigen-exposed T-lymphocyte may have either of two direct and opposite effects on B-lymphocytes depending on the subclass of T-lymphocyte. The major subclasses are the helper cell and the other is the suppressor cell. Helper T-lymphocytes are necessary for a complete B cell response to T-lymphocyte-dependent antigens. T-lymphocyte dependent antigens tend to be the more complex antigens such as bacterial proteins, virus proteins and other large complex proteins in general.

Unlike helper T-lymphocytes, suppressor T-lymphocytes block the development of effector B and T lymphocytes. Specific suppressor T-lymphocytes have now been demonstrated to play a large role in tolerance to many proteins, both in antibody and cell-mediated immune responses. In addition, genetic unresponsiveness to some antigens is due to the greater stimulation of suppressor T-lymphocytes than of helper T-lymphocytes by these antigens.

Thus, in the normal, healthy animal, the thymus is normally active only during the early years of life. During these early years of thymic activity, the thymus supplies the animal with the T-lymphocytes which will serve the animal for the rest of its life. In certain diseases, such as rheumatoid arthritis, the thymus may regain some activity during adult life. This demonstrates that the adult thymus retains capacity to function and that involution is not necessarily permanent. At least partial function might be restored if the appropriate agents were available.

Acquired T-lymphocyte deficiency diseases of adults are characterized by a depletion of circulating T-lymphocytes. The symptoms expressed in these diseases include an inability to mount a cell mediated immune response in response to an antigen challenge. An example of an acquired T-lymphocyte deficiency disease is acquired immune deficiency syndrome or AIDS.

AIDS is a disease caused by the human T-lymphocyte lymphotrophic virus (LAV or HTLV-III). The virus specifically attacks T-4 helper lymphocytes, a subgroup of T-lymphocytes that plays a major role in defending the body against infectious diseases. Depletion of this subset of lymphocytes is manifested by an increased incidence of opportunistic infections like Pneumocystis carinii and certain cancers. More specifically, the virus enters the T-lymphocyte and incorporates viral encoded DNA into the DNA of the host T-lymphocyte. As long as the infected T-lymphocyte remains inactivated, the virus will quietly remain in the DNA of the host cell. This will not kill the cell but may impair its function. When the infected T-lymphocytes are activated by stimuli such as a specific antigen, the viral DNA in the host DNA is expressed and produces new viral particles. The host T-lymphocyte is then killed and lysed, releasing new viral particles that can invade and kill other T-lymphocytes. The loss of T-4 lymphocytes is profound and occurs even faster than can be accounted for by direct viral killing of the cells. This has led some investigators to postulate that the infection somehow shuts off the production of T-4 lymphocytes. In any case, the thymus in the normal adult is no longer functioning and the killed T-lymphocytes cannot be replaced leaving the patient vulnerable to subsequent infections. Especially striking are recent studies of the thymuses of deceased AIDS patients ranging in age from 10 months to 42 years. AIDS victims have profound thymic involution; much more extensive than in age-matched patients who died of other causes.

The cure of a person with AIDS will probably require one agent to eliminate the virus and other agents to cause the body to replace T cells that have been killed by the virus. The first step is to eliminate the AIDS virus from the patient. This will have to be supported by other therapies to induce restoration of immune function. Studies to date with macrophage activating agents, interferon inducers and lymphokines have been disappointing, possibly because their targets, T-lymphocytes, do not exist in sufficient numbers. Interleukin 2 restores the function of one subset of non T-cells (natural killer cells) but has no effect on a host of other serious defects. More drastic measures can be performed. One potential method of restoring the immune system is by transplanting bone marrow from healthy donors. However, this is a dangerous procedure. It may produce lethal graft versus host disease unless the patient's donor is an identical twin.

Another area where them is a need to re-establish not only the immune system, but also the hematopoietic system, is in total body irradiation for treatment of leukemia. When a patient undergoes high dose total body irradiation, the entire immune system is destroyed. The usual treatment after the irradiation is to perform a bone marrow transplant with marrow from a close relative. If the transplant is successful, the new marrow will produce new cells, thereby restoring both red blood cells and white blood cells to the body. However, this is a dangerous treatment that is successful in only a fraction of the cases. Localized radiation of tumors and several types of chemotherapy also produce suppression of T-cell mediated immunity.

What is needed is a safe and effective method of re-establishing T-lymphocyte function. One method of re-establishing T-lymphocyte function is by treating existing T-lymphocytes so that they resume their normal immune functions. Agents that have been shown to be effective in certain situations in stimulating T-lymphocytes include macrophage activating factors, interferon inducing agents, lymphokines and cytokines. However, in a disease such as AIDS or in the case of irradiation in which the T-lymphocyte population has been destroyed, this type of treatment is not effective because the number of T-lymphocytes is severely depleted. In these cases, an effective method of causing the thymus to produce new T-lymphocytes would be the treatment of choice. However, to date, there is no effective treatment that will cause the thymus to reverse the process of involution and produce new T-lymphocytes.

AUTOIMMUNE DISEASES

Autoimmune diseases are characterized by the development of an immune reaction to self components. Normally, tissues of the body are protected from attack by the immune system; in autoimmune diseases there is a breakdown of the self-protection mechanisms and an immune response directed to various components of the body ensues. Autoimmune diseases are for the most part chronic and require life long therapy. The number of recognized autoimmune diseases is large and consists of a continum ranging from diseases affecting a single organ system to those affecting several organ systems. With increased understanding of the molecular basis of disease processes, many more diseases will likely be found to have an autoimmune component. Specific examples of autoimmune diseases are presented below.

| Spectrum of Autoimmune Diseases | |
|---|---|
| Organ Specific | Hashimoto's thyroiditis |
| | Graves' disease |
| | Addison's disease |
| | Juvenile diabetes (Type I) |
| | Myasthenia gravis |
| | Pemphigus vulgaris |
| | Sympathetic opthalmia |
| | Multiple sclerosis |
| | Autoimmunehemolytic anemia |
| | Active chronic hepatitis |
| | Rheumatoid arthritis |
| Non-organ specific | Systemic lupus erythematosus |

Systemic lupus erythematosus (SLE) is an inflammatory, multisystem disease characterized clinically as a relapsing disease of acute or insidious onset that may involve any organ in the body. Clinically, symptoms are due to disease affecting the skin, kidneys, serosal membranes, joints and heart. Anatomically, all sites have in common vascular lesions with fibrinoid deposits and immunologically, the disease involves antibodies of autoimmune origin, especially antinuclear antibodies (ANA). The ANA are directed against both DNA and RNA. Autoantibody development appears to be multifactorial in origin, involving genetic, hormonal, immunologic and environmental factors.

The morphologic changes seen in organs result from the formation of circulating immune complexes and their deposition in a variety of tissues. Although many organs can be affected, some are affected more than others. Lesion of joints, the kidneys, heart, and serous membranes are responsible for most of the clinical signs. The course of SLE is extremely variable and unpredictable. An acute onset with progressive downhill course to death within months can occur. The usual course however, is characterized by flare-ups and remissions spanning a period of years or even decades. It usually arises in the second or third decades of life, but may become manifest at any age.

Acute attacks are usually treated by adrenocortical steroids or immunosuppressive drugs. These drugs often control the acute manifestations. With cessation of therapy the disease usually reexacerbates. The prognosis has improved in the recent past; approximately 70 to 80% of patients are alive 5 years after the onset of illness and 60% at 10 years. Lifelong therapy is required to control the disease.

At one time SLE was considered to be a fairly rare disease. Better methods of diagnosis and increased awareness that it may be mild and insidious have made it evident that its prevalence may be as high as 1 case per 10,000 population. There is a strong female preponderance—about 10 to 1.

Rheumatoid arthritis is a systemic, chronic, inflammatory disease that affects principally the joints and sometimes many other organs and tissues throughout the body. The disease is characterized by a nonsuppurative proliferative synovitis, which in time leads to the destruction of articular cartilage and progressive disabling arthritis. The disease is caused by persistent and self-perpetuating inflammation resulting from immunologic processes taking place in the joints. As is the case with most autoimmune diseases, the trigger that initiates the immune reaction remains unidentified. Both homoral and cell mediated immune responses are involved in the pathogenesis of rheumatoid arthritis. The majority of patients have elevated levels of serum immunoglobulins and essentially all patients have an antibody called rheumatoid factor (RF) directed against a component of another antibody class.

The key event in the pathogenesis of the arthritis is the formation of antibodies directed against other self antibodies. Why these antibodies are formed is unknown at present. It has been suggested that the process is initiated by the formation of antibodies or immunoglobulins against an unknown antigen, possibly an infectious agent. When the antibodies combine with the antigen, conformational changes occur in a portion of the antibody molecule creating new antigenic determinants. The appearance of new determinants evokes an antibody response against the antibody molecule and results in the formation of anti-immunoglobulin antibodies or rheumatoid factor. T cells may also be involved in the pathogenesis of rheumatoid arthritis. A large number of T cells are found in the synovial membrane, outnumbering B cells and plasma cells. Additionally, procedure to decrease the population of T cells (such as draining the thoracic duct), result in remission of symptoms.

The most destructive effects of rheumatoid arthritis are seen in the joints. Classically, it produces symmetric arthritis, which principally affects the small joints of the hands and feet, ankles, knees, wrists, elbows, shoulders, temporomandibular joints and sometimes the joints of the vertebral column. The clinical course is highly variable. After approximately 10 years, the disease in about 50% of the patients becomes stabilized or may even regress. Most of the remainder pursue a chronic, remitting, relapsing course. After 10 to 15 years, approximately 10% of patients become permanently and severely crippled. The disease usually has its onset in young adults but may begin at any age and is 3 to 5 times more common in women than in men.

Rheumatoid arthritis is a very common disease and is variously reported (depending on diagnostic criteria) to affect 0.5 to 3.8% of women and 0.1 to 1.3% of men in the United States.

Multiple sclerosis is another disease that is thought to be caused by autoimmune mechanisms. The cause of multiple sclerosis is unknown but seems to be multifactorial. Susceptibility or resistance may be genetically determined; something in the environment interacts with the human host at the proper age to cause biochemical and structural lesions in the central nervous system. The systemic immune response and the response of the central nervous system become involved. Although the cause and pathogenesis of multiple sclerosis are unknown, it is widely believed that immune abnormalities are somehow related to the disease. Three possible mechanisms have been postulated: infection, autoimmunity, and a combination of the two. Suppression or modulation of the immune responses may be the key.

The graphic distribution of multiple sclerosis indicate that the disease is acquired from an environmental factor. Approximately 200 studies of the geographic distribution of multiple sclerosis have been conducted and have shown that regions of high prevalence (30 to 80 cases per 100,000 population) in northern Europe between 65 and 45 degrees north latitude and in the northern United States and southern Canada, as well as in southern Australia and New Zealand. In contrast, regions of low risk, including most of Asia and Africa, have a prevalence of 5 or fewer cases per 100,000.

Myasthenia gravis is an autoimmune disorder caused by antibodies directed against the acetylcholine receptor of skeletal muscle. Present information indicates at least three mechanisms whereby acetylcholine receptor antibody may interfere with neuromuscular transmission and thus induce myasthenia gravis. Acetylcholine receptor antibody may interfere (directly or indirectly) with acetylcholine receptor function. In both experimental allergic myasthenia gravis and human myasthenia gravis, the extent of acetylcholine receptor loss parallels the clinical severity of the disease, suggesting that acetylcholine receptor antibody-induced acceleration of acetylcholine receptor degradation is important in the development of myasthema gravis. Complement-mediated destruction of the postsynaptic region is the third possible cause. Other disorders, especially those presumed to be autoimmune in origin, can occur in association with myasthenia gravis. Thyroid disease, rheumatoid arthritis, systemic lupus erythematosus, and pernicious anemia all occur more commonly with myasthenia gravis than would be expected by chance.

The prevalence of myasthenia gravis in the United States is one per 20,000.

The foundation of therapy of autoimmune diseases is treatment with immunosuppressive agents. The basis for this therapy is attenuation of the self-directed immune response with the primary aim being to control symptoms of the particular disease. The drugs utilized to achieve this aim are far from satisfactory, in that adverse side effects are numerous and control of the disease is many times difficult to achieve. The problem is compounded by the chronicity of the disease with effective therapy becoming more difficult with time. An indication of the severity of particular diseases is seen in the willingness to accept greater risks associated with therapy as the disease progresses. Currently available therapy is distinctly non-selective in nature, having broad effects on both the humoral and cell mediated arms of the immune system. This lack of specificity can limit the effectiveness of certain therapeutic regimens. The main groups of chemical immunosuppressives are alkylating agents, antimetabolites, corticosteroids, and antibiotics, each will be discussed briefly.

The corticosteroids, also called adrenocorticosteroids, are fat-like compounds produced by the outer layer or cortex, of the adrenal gland. The adrenal cortex is an organ of homeostasis influencing the function of most systems in the body. It is responsible for adaptation of the body to a changing environment. Therapeutic use of the corticosteroids for autoimmune disease is based on their two primary effects on the immune system, anti-inflammatory action and destruction of susceptible lymphocytes. They also effect a redistribution of lymphocytes from peripheral blood back to the bone marrow. The use of corticosteroids is not without adverse side effects however, particularly during the course of life-long treatment which is required for many of the autoimmune diseases. Major side effects of steroids are:
1. Cushing syndrome
2. Muscle atrophy
3. Osteoporosis
4. Steroid induced diabetes
5. Atrophy of the adrenal glands
6. Interference with growth
7. Susceptibility to infections
8. Aseptic bone necrosis
9. Cataract development
10. Gastric ulcer
11. Steroid psychosis
12. Skin alterations
13. Nervous state accompanied by insomnia Attempts to minimize side effects incorporate alternate day or less frequent dosage regimens.

A recently developed immunosuppressive agent is the antibiotic cyclosporin A. The antibiotic has greatest activity against T cells and does not seem to have much direct effect on B cells. The drug is being evaluated for the treatment of autoimmune diseases for which it shows some promise. Side effects include hair growth, mild water retention, renal toxicity, and, in older patients, nervous system disorders symptoms have been observed.

Other drugs are used alone or in combination with those listed above and include gold salts and antimalarials, such as chloroquine. Another class of drugs, the nonsteroidal anti-inflammatory drugs are used extensively in arthritis. These drugs provide analgesia at low doses and are anti-inflammatory after repeated administration of high doses. Nonsteroidal anti-inflammatory drugs all act rapidly and their clinical effects decline promptly after cessation of therapy. They do not prevent the progression of rheumatoid arthritis and do not induce remissions. Immunostimulants, such as levamisol have also been used in many autoimmune diseases but side effects have generally limited their use.

GROWTH PROMOTING COMPOUNDS

With an ever-increasing world demand for food, there is constant pressure to increase the rate of production of food. In the early 1950s, researchers unexpectedly discovered that an antibiotic ingredient in chicken mash was a "growth factor." The finding drastically changed the nation's livestock and poultry production and was an economic boon for pharmaceutical companies. Feed animals are now raised under highly controlled conditions and receive specialized feed with a variety of growth promoting additives.

Routine antibiotic administration to animals has become almost universal since the discovery that the addition of small amounts of antibiotics such as penicillin, tetracycline and sulfamethazine, to animal feed increases the growth of pigs and cattle. In 1979, about 70% of the beef cattle and veal, 90% of the swine, and virtually 100% of broilers reared in the United States consumed antibiotics as part of their daily feed. This use, accounting for nearly 40% of antibiotics sold in the United States, is estimated to save consumers $3.5 billion a year in food costs.

Animals raised under modern conditions optimized for growth promotion receive rations containing high proportions of protein, usually in the form of soybean or cottonseed meal, and high percentages of grains such as corn or milo, a type of sorghum. Feed additives which have been used include such hormones as diethyl-stilbesterol, which also increases the rate of weight gain, and tranquilizers that prevent the effects of the stress brought on by confinement conditions from causing disease or weight loss.

Cattle ordinarily require 10 pounds of feed to produce one pound of weight gain. Under optimal growth promoting conditions and with enriched feed they gain one pound with only 6 pounds of feed.

Modern farming has greatly reduced the labor required to raise farm animals. In broiler chicken raising, where intensive methods have had the most dramatic effect, it took 16 hours of labor to raise a flock of 100 broilers in 1945; in 1970 that figure was reduced to 1.4 labor hours, in part because of the use of automated confinement facilities and associated advances in breeding and nutrition.

Although hormones and antibiotics have greatly increased the rate of growth of food animals, the use of such additives has not been without problems. One of the hormones that is commonly used as a growth stimulant, diethyl stilbesterol or DES, has been shown to be a carcinogen and has been banned from further use in most countries.

When antibiotics are mixed in animal feed, the compounds are spread throughout the environment exposing microorganisms to the antibiotics. The constant exposure of the microorganisms to antibiotics puts biological pressure on the microorganisms to develop a resistance to the antibiotics. This can result in a microorganism that is resistant to antibiotics and causes especially severe and difficult to treat infections.

An antibiotic-resistant microorganism is potentially a serious pathogen because it is difficult to control. If the organism causes an infection in an animal or in man, the infection may not be controlled with conventional antibiotics. If the infection is serious, there may not be time to determine which antibiotics are effective against the infecting bacteria. The problem has been especially serious when antibiotic resistant organisms in meat are consumed by people who themselves take antibiotics for treatment of disease. Antibiotics inhibit many of the normal microorganisms in the respiratory and gastrointestinal tracts. This allows the resistant ones to proliferate rapidly and produce more serious disease. The combination of antibiotic resistant organisms from food and ineffective antibiotic treatment of people has caused most of the deaths due to Salmonella food poisoning reported in the United States in the past several years.

As a result of the increasing appearance of antibiotic resistant bacteria in feed lots and several serious epidemics caused by antibiotic resistant bacteria, there is increasing governmental pressure to ban the use of antibiotics in animal feed. Consequently, there is an immediate and increasing need for new, safe and effective growth stimulators of farm animals.

REDUCING ENTERIC MICROORGANISMS

While many enteric microorganisms are beneficial to their host and reside in the host's gut without adverse consequence, many other enteric microorganisms are pathogenic and cause various and often sever disease states. For example, typhoid fever is caused by Salmonella, bacillary dysentery is caused by Shigella, and cholera is caused by Vibrio. These disease states remain a major public health threat in lesser developed countries. One approach to managing these diseases would be to treat patients, either before or after manifestation of disease symptoms, to reduce the number of microorganisms in the gut.

Additionally, the prevalence of Salmonella in animals, particularly poultry such as chickens, turkeys, pheasant, quail, geese, and duck, constitutes a constant source of expense to the farming and food industries and a health threat to consumers.

Further, pet fecal odor is a significant problem, particularly for house bound pets such as cats. Fecal odor is caused by certain intestinal microorganisms, and is diminished or eliminated if odor-producing microorganisms are reduced in the intestinal tract of the pet.

Consequently, there is an urgent and immediate need for compositions and methods for reducing enteric microorganisms and pathogens in humans, in farm animals, particularly Salmonella in poultry such as chickens, and in household pets.

ANTITUMOR COMPOUNDS

Malignant, or cancerous, tumors are defined by their invasion of local tissue and their ability to spread or metastasize to other parts of the body. The incidence of tumors is high; it is the second leading cause of death in both children and adults. A malignant tumor, by definition, always kills (unless treated) because of its invasive and metastatic characteristics. The tumor grows locally by encroachment into the normal tissues surrounding it. The tumor spreads to distant sites by the breaking off of malignant cells. These cells then move through the blood and lymphatic systems, attach themselves, and begin to grow as new colonies.

The factors controlling tumor growth are as poorly understood. Tumors in laboratory animals may be transplanted to a second host using only a single tumor cell. This facility suggests that only one normal cell need become transformed (cancerous) for tumor growth to begin. It is thought, however, that many transformed cells die or remain latent or dormant for extended periods before successful tumor growth is established. Tumors have been experimentally induced in animals by chemical, physical, and viral agents, and by radiation and chronic irritation.

Leukemia is a term given to tumors of the blood-forming organs. The acute and chronic leukemias, together with the other types of tumors of the blood, bone marrow cells (myelomas), and lymph tissue (lymphomas), cause about 10% of all cancer deaths and about 50% of all cancer deaths in children and adults less than 30 years old. At least 4 million people now living are expected to die from these forms of cancer, assuming them are no major advancements made in the treatment of these diseases.

Conventional treatment regimens for leukemia and for other tumors include radiation and drugs or a combination of both. In addition to radiation, the following drugs, usually in combinations with each other, are often used to treat acute leukemias: vincristine, prednisone, methotrexate, mercaptopurine, cyclophosphamide, and cytarabine. In chronic leukemia, for example, busulfan, melphalan, and chlorambucil can be used in combination. All of the conventional anti-cancer drugs are highly toxic and tend to make patients quite ill while undergoing treatment. Vigorous therapy is based on the premise that unless every leukemic cell is destroyed, the residual cells will multiply and cause a relapse.

Most of the conventional chemotherapeutic drugs that are being used in tumor therapy do not specifically kill tumor cells. Reliance is placed on the fact that, in most cancers, the cancerous cells grow faster than normal cells and will therefore utilize more of the toxic chemotherapeutic drug thereby specifically killing the cancer cell. Administration of the conventional chemotherapeutic drugs requires careful attention to the amount and concentration of the drug or combination of drugs so that the cancer cells will be killed but normal cells will survive. For this mason, it is difficult to kill all cancerous cells by conventional chemotherapy.

What is needed are compounds that will specifically and completely kill cancerous cells while not effecting normal cells. Ideally, the new compounds would take advantage of physical characteristics inherent only in the tumor cell. For example, a tumor cell may be more sensitive than normal cells to changes in ion concentrations within the cell. If a compound could detrimentally vary the internal ion concentrations of the tumor cells, then the compound could specifically kill the tumor cell while not adversely affecting normal cells.

IONOPHORIC COMPOUNDS

Ionophores are defined as substances capable of interacting stoichoimetrically with metal ions so as to transport the ions across a hydrophobic barrier such as a cell membrane.

It has been generally accepted that cell membranes consist of a phospholipid bilayer interspersed with globular protein molecules. The hydrophilic phosphate portions of the phospholipia are oriented at the outer edges of the membrane while the hydrophobic lipid portions face toward the center. The cell membrane is selectively permeable and will permit the entry of water, certain nutrients and essential metal ions to pass freely into the cell when needed. However, due to the double layer of nonpolar lipids in its center, the membrane is normally impermeable to highly polar molecules.

Different ionophores often have an affinity for one ion or one group of ions over another. The ions most commonly transported across cell membranes include $Na^+$, $K^+$, $Li^+$, $Rb^+$, $Cs^+$, $Ca^{+2}$, $Mg^{+2}$, $Ba^{+2}$, $Cu^{+2}$, $Fe^{+2}$, $Ni^{+2}$, and $Zn^{+2}$. For example, the negatively charged fungal antibiotic ionophore A23187 selectively forms an electrically neutral "encounter complex" with positively charged calcium ions. This hydrophobic molecule is capable of moving across a number of different cell membranes, and once the complex enters the cell, the calcium ion is released. This increase in intracellular free calcium has been shown to stimulate the secretion of a variety of substances such as histamine from rodent mast cells and human basophils, amylase and insulin from the pancreas, the hormone vasopressin from the pituitary, the neurotransmitter dopamine from neurons, seratonin from platelets, and catecholamines from adrenal glands. In addition, the A23187 calcium ionophore has been shown to activate sea urchin eggs.

With an ever-increasing world demand for food, there is constant pressure to increase the efficiency of production of food. Ruminant nutritionists have long sought means to manipulate and improve the efficiency of ruminal fermentation. Dietary manipulation was initially used to achieve this goal, but during the last decade a number of active antibiotic compounds, produced by various strains of Streptomyces, were discovered which improve metabolic efficiency. Although originally administered to poultry as anticoccidials, these carboxylic polyether antibiotic compounds, including monensin, lasalosid, salinomycin and narasin, have been found to exhibit ionophoric activity.

Since their discovery, antibiotic ionophores have been used extensively as feed additives to increase the efficiency of the production of poultry and ruminants. Studies have indicated that, when ionophores are added to feed, the growth of pathogens and other microorganisms within the digestive tract is inhibited, thus enhancing the efficient utilization of nutrients in the feed.

The various antibiotic ionophores appear to improve the efficiency of conversion from grain to meat by increasing the efficiency of metabolism in the rumen, improving nitrogen metabolism, and by retarding feedlot disorders such as chronic lactic acidosis and bloat. These effects are caused by a shift in the rumen microflora from bacteria less efficient in fermenting ingested feed to more bacteria that are more efficient. The change in rumen microflora population is brought about by a differential susceptibility of the bacteria to ion flux across their membranes. This influx of ions causes the bacterial cells to swell and burst.

Although antibiotic ionophores have greatly increased the efficiency of production of feed animals, the use of such additives has not been without problems. When antibiotics are mixed in animal feed, the compounds are spread throughout the environment exposing microorganisms to the antibiotics. The constant exposure of the microorganisms to antibiotics causes a resistance to antibiotics which in turn causes infections which are especially severe and difficult to treat.

An antibiotic-resistant microoorganism is potentially a serious pathogen because it is difficult to control. If the organism causes an infection in an animal or in man, the infection may not be controlled with conventional antibiotics. If the infection is serious, there may not be time to determine which antibiotics are effective against the infecting bacteria. The problem has been especially serious when antibiotic resistant organisms in meat are consumed by people who themselves take antibiotics for treatment of disease. Antibiotics inhibit many of the normal microorganisms in the respiratory and gastrointestinal tracts. This allows the resistant ones to proliferate rapidly and produce more serious disease. The combination of antibiotic resistant organisms from food and ineffective antibiotic treatment of people has caused most of the deaths due to Salmonella food poisoning reported in the United States in the past several years.

It is believed that there is currently no single class of compounds that possess such a wide range of biological activities. Such a class of compounds would provide a new and powerful arsenal for the treatment of disease and for increasing the worlds food supply.

SUMMARY OF THE INVENTION

In accordance with the present invention, a new class of biologically-active copolymers capable of effecting biological systems in many different ways is provided. The biologically active copolymers of the present invention are capable of stimulating the growth of an organism, stimulating the motor activity of an organism, and stimulating the production of T-cells in the thymus, peripheral lymphoid tissue, and bone marrow cells of an animal.

The biologically active copolymers of the present invention also have a wide variety of effects on individual cells.

These compounds have ionophoric activity, i.e., they cause certain ions to be transported across cell membranes. The compounds can cause non-cytolytic mast cell degranulation with subsequent histamine release. In addition, it has been found that certain members of this class of biologically-active copolymers are capable of specifically killing certain cancer cell lines. The biologically active copolymers are also effective against certain microorganisms.

The biologically active copolymers of the present invention can be administered orally to animals to provide specific effects on certain microorganisms that reside in the gut of the animal. For example, certain biologically-active copolymers can be administered to chickens to kill various species of coccidia that cause coccidiosis. Additionally, biologically active copolymers are administered to humans or animals to reduce the number of microorganisms in the gut. A preferred use is administering the biologically active copolymers of the present invention to poultry to reduce the number of Salmonella and other microorganisms in the poultry gut.

The biologically-active copolymers can also be added to cattle feed to effect a change in the population of microorganisms normally resident in the rumen. Under normal conditions, the microorganisms digest the cellulose that is eaten by the cattle to the end-product methane. Methane is essentially unusable by the cattle. By administering the biologically-active copolymers of the present invention orally to the cattle, the copolymer differentially affects the rumen microorganisms so that there is a shift in the rumen population of microorganisms resulting in an increase in propionic acid production and a decrease in lactic acid and methane. Cattle are capable of using propionate in their own metabolism thereby increasing the efficiency of food conversion.

Biologic effects of the copolymers of the present invention vary with the structure of the polymer. The ability to modify the structure of these polymers to optimize particular biologic effects provides the potential to design synthetic compounds with a precision and ease not possible in other systems.

The biologically-active copolymer of the present invention comprises a copolymer of polyoxyethylene (POE) which is hydrophilic and polyoxypropylene (POP) which is hydrophobic. The block copolymer is built on a tetrafunctional ethylenediamine initiator. In the preferred embodiment of the biologically-active copolymers of the present invention, the block copolymers that comprise the biologically-active copolymers of the present invention have the following general formulas:

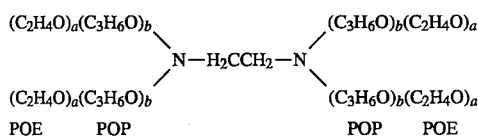

POE   POP               POP   POE wherein:

the mean aggregate molecular weight of the hydrophobe portion of the octablock copolymer consisting of polyoxypropylene $(C_3H_6O)_b$ (POP) is between approximately 5000 and 7000 daltons;

$a$ is a number such that the hydrophile portion represented by polyoxyethylene $(C_2H_4O)_a$ (POE) constitutes between approximately 10% and 40% of the total molecular weight of the compound; and $b$ is a number such that the polyoxypropylene $(C_3H_6O)_b$ (POP) portion of the total molecular weight of the octablock copolymer constitutes between approximately 60% and 90% of the compound.

In another embodiment of the biologically-active copolymer of the present invention, the block copolymer comprises a polymer of hydrophilic polyoxyethylene (POE) built on an ethylene diamine initiator. Polymers of hydrophobic polyoxypropylene (POP) are then added to the blocks of hydrophilic polyoxyethylene (POE). This results in an octablock copolymer with the following general formula:

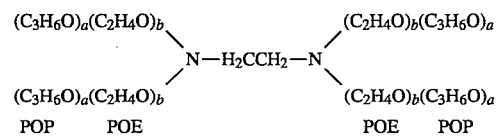

POP   POE               POE   POP wherein:

$a$ is a number such that the hydrophile portion represented by polyoxyethylene $(C_2H_4O)_a$ (POE) constitutes between approximately 10% to 40% of the total molecular weight of the compound;

the mean aggregate molecular weight of the hydrophobe portion of the octablock copolymer consisting of polyoxypropylene $(C_3H_6O)_b$ (POP) is between approximately 5000 and 7000 daltons; and $b$ is a number such that the polyoxypropylene $(C_3H_6O)_b$ (POP) portion of the total molecular weight of the octablock copolymer constitutes between approximately 60% and 90% of the compound.

The biologically-active copolymer of the present invention is usually administered by a subcutaneous, intravenous, or intramuscular injection of an effective amount of the copolymer into an animal or human. The biologically-active copolymer of the present invention can be taken orally if it is desired that the copolymer have an effect on alimentary canal microorganisms. Normally, very little of the copolymer is absorbed from the alimentary canal.

Accordingly, it is an object of the present invention to provide compounds that have a wide variety of biological activities.

Another object of the present invention is to provide compounds that can stimulate the T-cell immune system.

Another object of the present invention is to provide a compound that will stimulate the growth of the thymus in an adult animal.

Another object of the present invention is to provide compounds that can stimulate the production of bone marrow cells.

A further object of the present invention is to stimulate bone marrow and enhance recovery from radiation or other insults toxic to the bone marrow.

Another object of the present invention is to provide compounds that can accelerate and prolong growth.

Yet another object of the present invention is to provide compounds that can stimulate motor activity in animals and humans.

Another object of the present invention is to provide compounds that have ionophore activity.

Another object of the present invention is to provide compounds that can cause non-cytolytic mast cell degranulation.

Another object of the present invention is to provide compounds that can specifically kill certain tumor cell lines.

Another object of the present invention is to provide compounds that can kill or eliminate microorganisms that reside in the gut.

Another object of the present invention is to specifically immunosuppress an animal against an antigen or a hapten.

Yet another object of the present invention is to provide compounds that are capable of altering the metabolism of ruminant animals so that the efficiency of feed conversion is increased.

These and other objects, features and advantages of the present invention will become apparent after a review of the following detailed description of the disclosed embodiment and the appended claims.

DETAILED DESCRIPTION OF THE PREFERRED EMBODIMENT

The present invention comprises a class of biologically active copolymers which have a wide variety of biological functions which are useful in treating various pathological conditions in both humans and animals and which can also be used to increase the efficiency of food production.

The biologically-active copolymers of the present invention comprise a surface active compound with hydrophobic segments and a small proportion of hydrophile that is built upon an initiator compound. The initiator compound typically has one or more active hydrogens upon which the hydrophobic or hydrophilic polymer units are condensed. Compounds that can be used as initiators in producing the biologically active copolymers of the present invention include, but are not limited to, methylamine, ethylamine, propylamine, butylamine, amylamine, hexylamine, aniline, the alkylene polyamines, especially aliphatic primary diamines such as ethylenediamine, propylene diamine, diethylenetriamine, triethylenetetramine, tetraethylenepentamine, hexamethylene-diamine, phenylenediamine, and the like. Alkanolamines such as monoethanolamine, diethanolamine, triethanolamine, isopropanolamine, tri(t-propanol)amine, 2-amino-1-butanol, N-butyl-di(2-propanol)amine can also be used as initiators.

Furthermore, heterocyclic compounds containing a hetero nitrogen atom can be employed, such as piperazine, 2 methylpiperazine, 2,5-dimethylpiperazine, imidazimidazole, pyrazolidine, pyrazolidone, hydantoin, dimethyl hydantoin and the like. Hydroxyl amine and the hydroxylamine derivatives and aminophenol and aminophenol derivatives can also be used as initiators to produce the biologically active copolymers of the present invention.

The compositions of this invention are surface active mixtures of conjugated polyoxypropylene-polyoxyethylene compounds based on the reactive hydrogen compounds wherein chains of oxypropylene groups having a defined molecular weight are attached to the initiator of the reactive hydrogen compound at the sites of the reactive hydrogen atoms and wherein chains of oxyethylene groups are then attached to the ends of the oxypropylene chains. Alternatively, the chains of oxyethylene groups having a defined molecular weight can be attached to the initiator of the reactive hydrogen compound at the sites of the reactive hydrogen atoms and then chains of oxypropylene groups can be attached to the ends of the oxyethylene chains.

The compositions are prepared by condensing either ethylene oxide or propylene oxide with the reactive hydrogen on the initiator compound. After the first block of monomer units have been added to the initiator molecule, a second block of either propylene oxide or ethylene oxide is condensed with the reactive hydrogen on the end of the first block. It is to be understood that butylene oxide can be substituted, either all or part, for propylene oxide in the biologically active copolymers of the present invention.

It is to be noted that it is not necessary to use pure propylene oxide in producing the oxypropylene chains of the biologically active copolymers of the present invention. Small amounts, for example, up to 5 weight percent, of ethylene oxide can be included in the propylene oxide employed to prepare the hydrophobic reactive hydrogen compound-propylene oxide condensate. Likewise, the ethylene oxide condensed with the hydrophobic propylene oxide-reactive hydrogen compound condensate can also contain small amounts, such as up to about 5 weight percent, of propylene oxide.

It is further to be noted that when molecular weight is stated in this specification and claims, unless otherwise noted, there is meant the average theoretical hydrophobe molecular weight which equals the total of the grams of the propylene oxide employed per mole of reactive hydrogen compound. The end groups of polyether chains are hydroxyl groups. The number averaged molecular weight can be calculated from the analytically determined "OH Number" expressed in mg KOH/g sample. It should be understood that lo the absolute value of the molecular weight of a polydisperse compound can be different depending upon the methodology used to determine the molecular weight.

Alternatively, copolymers can be fractionated by a variety of methods, such as gel permeation chromatography, and analyzed for weight percent of oxyethylene and for unsaturation by proton NMR analysis. An example of such an analysis is as follows: Copolymer is dissolved in tetrahydrofuran at a concentration of 20 mg/mL. A Model 600E Powerline chromatographic system equipped with a column heater module, a Model 410 refractive index detector and Maxima 820 software package (all from Waters, Div. of Millipore, Milford, Mass.) is used to fractionate the copolymer. The chromatographic system is equipped with Ultrastyragel $10^3$ A and 500 A in series (Waters, Div. of Millipore, Milford, Mass.). Column size is 7.8 mm internal diameter by 30 cm. Precolumn filters #A-315 with removable 2 µm fits (Upchurch Scientific, Oak Harbor, Wash.) are used for protection of the columns. 200 µL (4 mg) of the copolymer in tetrahydrofuran is added to the column and the sample is run with the columns at 40° C. and the detector at 45° C.

All proton NMR analyses are performed in accordance with the NF procedure "Weight Percent Oxyethylene" on a Bruker 300 MHz instrument. The weight percent oxyethylene is calculated from the proton NMR spectra is used to determine.

It is well recognized in the field of alkylene oxide chemistry that the polyoxyalkylene compositions one obtains by condensing an alkylene oxide with a reactive hydrogen compound are actually mixtures of compounds rather than a single molecular compound. The mixture contains closely related homologues wherein the statistical average number of oxyalkylene groups equals the number of moles of the alkylene oxide employed and the individual members in the mixture contain varying numbers of oxyalkylene groups. Thus, the compositions of this invention are "mixtures" of compounds which are defined by molecular weight of the polyoxypropylene chains and weight percent of oxyethylene groups.

The biologically-active copolymers of the present invention comprise a surface active compound with four hydrophobic segments and a small proportion of hydrophile. Typical examples have eight segments or octablock structure with a core of either a hydrophobic or hydrophilic central structure and a hydrophilic or hydrophobic outer structure as shown in the following schematic structures.

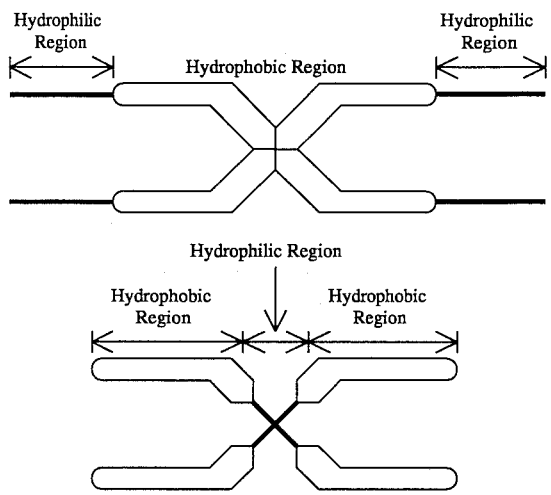

The entire molecule is poorly soluble in water and is either a nonionic or weakly cationic surface active agent. The steric configuration and physiochemical properties of the molecule, rather than the chemical nature of the constituent parts, are thought to be responsible for the biologic effects of the copolymer.

The biologically active compounds of the present invention comprise blocks of polyoxypropylene and polyoxyethylene built on an alkylenediamine initiator. The blocks of polyoxypropylene (POP) and polyoxyethylene (POE) have the following structures:

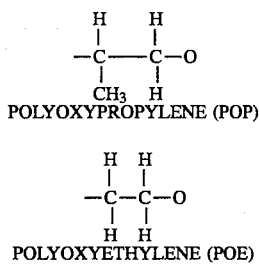

The polymer blocks are formed by condensation of ethylene oxide and propylene oxide onto a tetrafunctional ethylene diamine initiator at elevated temperature and pressure in the presence of a basic catalyst. There is some statistical variation in the number of monomer units which combine to form a polymer chain in each copolymer. The molecular weights given are approximations of the average weight of copolymer molecule in each preparation. A further description of the preparation of these block copolymers is found in U.S. Pat. No. 2,674,619 and U.S. Pat. No. 2,979,528. (Also see "A Review of Block Polymer Surfactants", Schmolka, I. R., *J. Am. Oil Chemists' Soc.*, 54:110–116 (1977) and *Block and Graft Copolymerization*, Volume 2 edited by R. J. Ceresa, John Wiley & Sons, New York (1976).

CHEMICAL STRUCTURE

In one embodiment of the biologically active copolymers of the present invention, the block copolymer comprises a polymer of hydrophobic polyoxypropylene (POP) built on an ethylenediamine initiator. Polymers of hydrophilic polyoxyethylene (POE) are then built on the block of hydrophobic polyoxypropylene (POP). This results in an octablock copolymer with the following general formula:

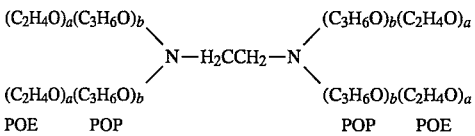

wherein:

the mean aggregate molecular weight of the hydrophobe portion of the octablock copolymer consisting of polyoxypropylene $(C_3H_6O)_b$ (POP) is between approximately 5000 and 7000 daltons;

a is a number such that the hydrophile portion represented by polyoxyethylene $(C_2H_4O)_a$ (POE) constitutes between approximately 10% to 40% of the total molecular weight of the compound;

b is a number such that the polyoxypropylene $(C_3H_6O)_b$ (POP) portion of the total molecular weight of the octablock copolymer constitutes between approximately 60% and 90% of the compound; and In another embodiment of the present invention, the block copolymer comprises a polymer of hydrophilic polyoxyethylene (POE) built on an ethylene diamine initiator. Polymers of hydrophobic polyoxypropylene (POP) are then built on the block of hydrophilic polyethylene (POE). This results in an octablock copolymer with the following general formula:

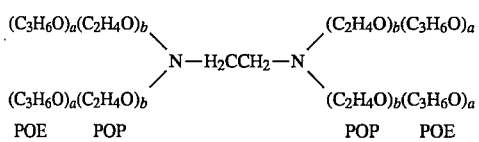

wherein:

The molecular weight of the hydrophobe portion of the octablock copolymer consisting of polyoxypropylene $(C_3H_6O)_b$ (POP) is between approximately 5000 and 7000 daltons;

a is a number such that the hydrophile portion represented by polyoxyethylene $(C_2H_4O)_a$ (POE) constitutes between approximately 10% and 40% of the total molecular weight of the compound;

b is a number such that the polyoxypropylene $(C_3H_6O)_b$ (POP) portion of the octablock copolymer constitutes between approximately 60% and 90% of the compound.

This type of polymer is called reverse copolymer because its structure is the reverse of octablock copolymers that have polyoxypropylene (POP) in the center flanked by blocks of polyoxyethylene (POE).

The octablock copolymers comprising the biologically active copolymers of the present invention include, but are not limited to, the block copolymers Tetronic® and reverse Tetronic® manufactured by the BASF Corporation (BASF Corporation, Parsippany, N.J.). These include copolymers wherein a is a number such that the hydrophile portion represented by polyoxyethylene $(C_2H_4O)_a$ (POE) constitutes between approximately 5% and 20% of the total molecular weight of the compound;

b is a number such that the polyoxypropylene $(C_3H_6O)_b$ (POP) portion of the octablock copolymer constitutes between approximately 80% and 95% of the compound.

A preferred biologically active copolymer is the octablock copolymer T110R1 (BASF Corporation, Parsippany, N.J.)

which corresponds to the following formula:

$$(C_3H_6O)_a(C_2H_4O)_b \diagdown \diagup (C_2H_4O)_b(C_3H_6O)_a$$
$$N-H_2CCH_2-N$$
$$(C_3H_6O)_a(C_2H_4O)_b \diagup \diagdown (C_2H_4O)_b(C_3H_6O)_a$$
$$\text{POE} \quad \text{POP} \qquad \text{POP} \quad \text{POE}$$

wherein:

The mean molecular weight of the hydrophobe portion of the octablock copolymer represented by polyoxypropylene $(C_3H_6O)_b$ (POP) is approximately 5,220 daltons;

a is a number such that the hydrophile portion represented by polyoxyethylene $(C_2H_4O)_a$ (POE) constitutes approximately 10% of the compound by weight; and b is a number such that the polyoxypropylene $(C_3H_6O)_b$ (POP) portion of the octablock copolymer constitutes approximately 90% of the compound by weight.

A preferred biologically active copolymers is the octablock copolymer T130R2 (BASF Corporation, Parsippany, N.J.) which corresponds to the following formula:

$$(C_3H_6O)_a(C_2H_4O)_b \diagdown \diagup (C_2H_4O)_b(C_3H_6O)_a$$
$$N-H_2CCH_2-N$$
$$(C_3H_6O)_a(C_2H_4O)_b \diagup \diagdown (C_2H_4O)_b(C_3H_6O)_a$$
$$\text{POP} \quad \text{POE} \qquad \text{POE} \quad \text{POP}$$

wherein:

The mean molecular weight of the hydrophobe portion of the octablock copolymer represented by polyoxypropylene $(C_3H_6O)_b$ (POP) is approximately 5750 daltons;

a is a number such that the hydrophile portion represented by polyoxyethylene $(C_2H_4O)_a$ (POE) constitutes approximately 20% of the compound by weight; and b is a number such that the polyoxypropylene $(C_3H_6O)_b$ (POP) portion of the octablock copolymer constitutes approximately 80% of the compound by weight.

Another preferred embodiment of the biologically active copolymers of the present invention is the compound designated T1501 (BASF Corporation, Parsippany, N.J.) which corresponds to the following formula:

$$(C_2H_4O)_a(C_3H_6O)_b \diagdown \diagup (C_3H_6O)_b(C_2H_4O)_a$$
$$N-H_2CCH_2-N$$
$$(C_2H_4O)_a(C_3H_6O)_b \diagup \diagdown (C_3H_6O)_b(C_2H_4O)_a$$
$$\text{POE} \quad \text{POP} \qquad \text{POP} \quad \text{POE}$$

wherein:

the mean molecular weight of the hydrophobe portion of the octablock copolymer represented by polyoxypropylene $(C_3H_6O)_b$ (POP) is approximately 6750 daltons;

a is a number such that the hydrophile portion represented by polyoxyethylene $(C_2H_4O)_a$ (POE) constitutes approximately 10% of the compound by weight; and b is a number such that the polyoxypropylene $(C_3H_6O)_b$ (POP) portion of the octablock copolymer constitutes approximately 90% of the compound by weight.

The most preferred embodiment of the biologically active copolymers of the present invention is the octablock copolymer T150R1 (BASF Corporation, Parsippany, N.J.) which corresponds to the following formula:

$$(C_3H_6O)_a(C_2H_4O)_b \diagdown \diagup (C_2H_4O)_b(C_3H_6O)_a$$
$$N-H_2CCH_2-N$$
$$(C_3H_6O)_a(C_2H_4O)_b \diagup \diagdown (C_2H_4O)_b(C_3H_6O)_a$$
$$\text{POP} \quad \text{POE} \qquad \text{POE} \quad \text{POP}$$

wherein:

The mean molecular weight of the hydrophobe portion of the octablock copolymer represented by polyoxypropylene $(C_3H_6O)_b$ (POP) is approximately 6750 daltons;

a is a number such that the hydrophile portion represented by polyoxyethylene $(C_2H_4O)_a$ (POE) constitutes approximately 10% of the compound by weight; and b is a number such that the polyoxypropylene $(C_3H_6O)_b$ (POP) portion of the octablock copolymer constitutes approximately 90% of the compound by weight.

BIOLOGICAL ACTIVITIES

Although not wanting to be bound by the following theory, it is believed that the biologically active polymers of the present invention act by the following mechanism:

Investigators have demonstrated hormone-mediated interactions between the thymus and the central nervous system. The biologically active copolymers of the present invention are capable of affecting this relationship. It is believed that the present invention acts by mimicking the conformation and physiochemical properties of natural hormones and neuropeptides. The biologic responses induced by the biologically active copolymers of the present invention include:

1. Stimulation of rate and duration of growth of animals;

2. Gross morphologic changes in the uterus and adrenal glands;

3. Increased motor activity including excessive grooming;

4. Diuresis;

5. Noncytolytic release of histamine from mast cells by a temperature, calcium, energy dependent mechanism which is similar to from that of somatostatin and ACTH.

It is believed that there is a structural analogy between the biologically active copolymers and hormones, such as somatostatin, adrenocorticotropic hormone (ACTH), and β-endorphin. These peptides have in common a sequence of basic amino acids adjacent to spans of hydrophobic amino acids. These features are thought to be essential for function. Interaction of the oligoamine residues with cell surface anions and stabilization by adjacent hydrophobic moieties initiates the molecular program resulting in effector functions of the peptide. The block polymers have the same structural features: a central basic ethylenediamine flanked by spans of hydrophobic polyoxypropylene (POP). By means of inhibition with monovalent amines, we have evidence that the central ethylenediamine groups function like the basic moieties of peptide hormones in stimulating release of histamine from mast cells.

In vitro studies provide direct evidence that the biologically active copolymers of the present invention act in a manner analogous to somatostatin and ACTH. Mast cells have been used as a model to study receptor mediated mechanisms through which these hormones induce their biological receptor mediated mechanisms. Minute quantities of the polymers cause histamine release from mast cells by a temperature dependent process which requires energy and calcium and can be blocked by specific inhibitors in a manner very similar to that of somatostatin and ACTH.

Both agonistic and antagonistic effects of hormones may be elicited by the polymers. Biologic effects of the polymers vary with the structure of the polymer. The ability to modify the structure of these polymers to optimize particular biologic effects provides potential to design synthetic drugs with a precision and ease not possible in other systems.

Many chelating agents, such as ethylene-diaminetetraacetic acid (EDTA) consist of oligoamine sites flanked by hydrogen bonding groups. The addition of flanking hydrophobic moieties produces ionophores which are able to transport ions across lipid containing membranes. The compounds of the present invention have this general structure and can act as ionophores transporting actions across artificial membranes. Consequently, the compounds of the present invention represent a new chemical type of ionophore. Some neuropeptide hormones (e.g., substance P) have ionophore activity.

The biologically-active copolymers of the present invention are also effective in causing the cortex of the thymus to begin producing new T-lymphocytes thereby replenishing the immune system with these vital regulatory cells. The copolymers also induce proliferation of large numbers of post-thymic T-cells in the lymph nodes and other peripheral lymphoid tissues.

The biologically active copolymers of the present invention also exhibit adjuvant and inflammatory activities which vary depending on the length and arrangement of the blocks of polyoxyethylene and polyoxypropylene. The reverse octablock copolymers cause active, calcium dependent histamine release from murine mast cells in vitro and the efficacy of histamine release is related to inflammatory activity in vivo.

The biologically active copolymers of the present invention when injected into an animal or a human with an antigen are effective in specifically immunosuppressing the animal or human against that antigen. For purposes of definition, antigens can be broken down into two groups: immunogens and haptens.

Immunogens are compounds which, when introduced into a mammal, will result in the formation of antibodies. Representative of the immunogens are proteins, glycoproteins and nucleoproteins, such as peptide hormones, serum proteins, complement proteins, coagulation factors, and viral or bacterial products. The following is a partial list of representative immunogens.

| | |
|---|---|
| proteins | glycoproteins |
| nucleoproteins | peptide hormones |
| serum proteins | complement proteins |
| coagulation factors | microbiocidal products |
| viral products | bacterial products |
| fungal products | specific immunogens |
| albumin | angiotensin |
| bradykinin | calcitonin |
| carcinoembryonic antigen | chloriomamotropin |
| chorogonadotropin | corticotropin |
| erythropoietin | Factor VIII |
| fibrinogen | alpha-2-H globulin |
| follitropin | gastrin |
| gastrin sulfate | glucagon |
| gonadotropin | haptoglobin |
| Hepatitis B surface antigen | immunoglobulins |
| insulin | lipotropin |
| melanotropin | oxytocin |
| pancreozymin | placental lactogen |
| prathryin | proangiotensin |
| prolactin | somatotropin |
| somatomadin | somatostatin |

| -continued | |
|---|---|
| thryrotropin | vasotocin |
| thymopoietin | vasopressin |
| alpha-1-fetoprotein | alpha-2-H globulin |
| myelin | myelin basic protein |

Haptens are compounds which, when bound to an immunogenic carrier and introduced into a chordate, will elicit formation of antibodies specific for the hapten. Representative of the haptens are steroids such as estrogens and cortisones, low molecular weight peptides, other low molecular weight biological compounds, drugs such as antibiotics and chemotherapeutic compounds, industrial pollutants, flavoring agents, food additives, and food contaminants, and/or their metabolites or derivatives.

The biologically active copolymers of the present invention also are active in reducing enteric microorganisms in the gut of humans and animals. Enteric microorganisms and pathogens such as, but not limited to, Salmonella, Escherichia, Klebsiella, Enterobacter, Pseudomonas, Serratia, Shigella, Campylobacter, Proteus, Edwardsiella, Yersinia, Eimeria and Vibrio are reduced in the gut by treatment with the biologically active copolymers of the present invention.

For example, Salmonella counts in the gut of chickens or other animals are reduced by administering an effective amount of the copolymers of the present invention to the chicken or other animal. A preferred method of administration for treatment to reduce enteric microorganisms in humans and animals is oral ingestion. For example, the copolymers can be administered to animals by admixing the copolymers with standard feed mixtures, which subsequently are fed to animals to be treated.

It is to be understood that the preferred biologically-active compound may differ in structure depending upon the biological activity that one desires to elicit.

ADMINISTRATION OF THE BIOLOGICALLY ACTIVE COPOLYMERS

The biologically-active copolymers of the present invention are generally poorly soluble in water. Although the compounds can be injected into an animal or human in aqueous media, it is preferable that the biologically-active copolymers of the present invention be injected as an oil-in-water or water-in-oil emulsion. A mineral oil or other oily substance such as Drakeol 6VR or Drakeol 5 (Penreco, Butler, Pa.) can be used as the oil phase of the emulsion. The aqueous phase can be physiologic phosphate buffered saline or other physiologic salt solution. The ratio of oil to water is preferably between approximately 80:20 and 1:100.

Typically, an oil-in-water emulsion is prepared by mixing between approximately 0.5 to 50 grams of the biologically active copolymers with 5.0 ml of mineral oil in a Potter-Elvehjim homogenizer. Next, 95.0 ml of phosphate buffered saline (0.85M sodium chloride, pH 7.3) containing 0.2% polyoxyethylene sorbitan monooleate (Tween 80, Atlas Chemical Industries, Wilmington, Del.) and 50 mg bovine serum albumin (BSA, Sigma Chemical. Co., St. Louis, Mo.) is added. The mixture is homogenized thoroughly to form a fine emulsion. The BSA and Tween 80 are used to stabilize the emulsion. It is to be understood that the method of preparing the emulsion, the proportions of oil and water and the type of oil used are not critical. An effective emulsion could be prepared by using a blender, by sonication or other means well known to those of ordinary skill in the art. It is to be further understood that other carriers, emulsifiers, aqueous solutions and adjuvants that are known to those of ordinary skill in the art can be used with the biologically active copolymers of the present invention.

Water-in-oil emulsions are prepared as follows. A stock oil-emulsifier mixture is prepared by blending mineral oil with approximately 5% to 10% of a water-in-oil emulsifier. A mixture of 94.5% oil (Drakeol, Penreco, Butler, Pa.), 4.5% Sorbitan monooleate (Span 80, Atlas Chemical Industries, Wilmington, Del.) and 0.5% polyoxyethylene sorbitan monooleate (Tween 80, Atlas Chemical Industries, Wilmington, Del.) is commonly used. A commercial blend, Freund's incomplete adjuvant, (Difco, Detroit, Mich. or Sigma Chemical, St. Louis, Mo.) is also suitable. Approximately 0.5 to 5.0 grams of the biologically active copolymers is added to either 60 ml of the oil-emulsifier mixture or to 40 ml of a physiologic saline solution similar to that used in the oil-in-water emulsion described above. The oil-emulsifier mixture is placed in a blender. The physiologic salt solution is added in three aliquots with vigorous homogenization to insure that a fine water-in-oil emulsion is prepared. Again, it is to be understood that the method of preparing the emulsion is not critical. Numerous variations of the composition of the aqueous and oil phases, their proportions and means of emulsification will be apparent to those skilled in the art and could be used with biologically active copolymers in practicing the invention.

The biologically active copolymers of the present invention are effective with only one injection of compound being administered to an animal. However, in certain cases, subsequent injections may be necessary to achieve maximum stimulation of the immune system or other desired effect. The mode of injection can be subcutaneous, intramuscular or intravenous. A preferred mode of injection is subcutaneous. Intravenous injection is hazardous because of the toxic effects of embolic emulsions.

The optimum amount of the biologically active copolymers in an injection varies with the size of the animal being treated. With animals such as rats or mice, the optimum amount of biologically active copolymers is between approximately 0.5 and 5 mg per animal. With larger animals a larger quantity of biologically active copolymers is required in the injection for optimum results. With humans, cattle or swine, the dose varies with the age, size and condition of the individual but approximates 5 to 500 mg in most cases.

The following specific examples will illustrate the invention as it applies in particular to stimulating the immune system in mice and rats. It will be appreciated that other examples will be apparent to those of ordinary skill in the art and that the invention is not limited to these specific illustrative examples.

BRIEF DESCRIPTION OF THE FIGURES

FIG. 1 shows histamine release from mast cells that have been exposed to several copolymers of the present invention.

FIG. 2 shows influx of sodium ions into red blood cells that have been exposed to several copolymers of the present invention.

FIG. 3 shows the relationship between footpad swelling and sodium flux and several of the copolymers of the present invention.

FIG. 4 shows the effect of T150R1 on mouse thymus in vivo.

FIG. 5 shows the effect of the copolymer of the present invention on motor activity in rats.

FIG. 6 shows the differential tumoricidal activity of T150R1 on K-652 cells and HL-60 cells as measured by cell viability.

FIG. 7 shows the differential tumoricidal activity of T150R1 on K-652 cells and HL-60 cells as measured by tritiated thymidine uptake.

FIG. 8 shows the differential tumoricidal activity of T150R1 and T150R2 on K-652 cells and HL-60 cells as measured by release of lactic dehydrogenase.

FIG. 9 shows active immunosuppression by T150R1.

FIG. 10 shows adoptive immunosuppression by cells from a rat treated with T150R1.

FIG. 11 shows stimulation of thymus cell proliferation by T150R1 in Lewis rats as measured by increased number of cells.

FIG. 12 shows stimulation of thymus cell proliferation by T150R1 in Lewis rats as measured by increased in vivo incorporation of tritiated thymidine.

EXAMPLES

Example I - Mast Cell Degranulation

The mast cell degranulation activity of several of the copolymers of the present invention are shown in this Example. Block copolymers were obtained from BASF Corporation, Parsipanny, N.J., and are shown in the following Table A.

TABLE A

| Copolymer | Mean[a,b] Mol. Wt.[a] | Structure |
|---|---|---|
| T110R1 | 5,220 | N-$\underline{3}$-21 |
| T130R1 | 6,800 | N-$\underline{4}$-26 |
| T130R2 | 7,740 | N-$\underline{10}$-26 |
| T150R1 | 8,000 | N-$\underline{5}$-32 |
| T150R4 | 11,810 | N-$\underline{27}$-32 |
| T150R8 | 20,400 | N-$\underline{92}$-32 |

[a] Data from manufacturer
[b] Amine nitrogen followed by mean number of ethoxy units (underlined) followed by mean number of propyloxy units per linear chain The copolymers in Table A range in physical form from viscous liquids to flakes. Measurement of the liquid copolymers was made using a positive displacement piper based on a density approximately equal to that of water (range 1.01–1.03). Since the solubility of these materials in aqueous medium decreases with increasing temperature, all dilutions were made in cold (4° C.) buffer.

Mouse peritoneal mast cells were obtained by lavage from female $C_3H$ mice (Charles River, Wilmington, Mass.). For each experiment one or two animals were sacrificed using dry ice vapors and the peritoneal cavity injected with 10 ml ice cold Dulbecco's phosphate-buffered saline (hereinafter PBS) (Gibco, Grand Island, N.Y.) containing 10 U/ml heparin. The peritoneum was massaged for 30 seconds and the fluid withdrawn. Cells were washed twice in PBS and counted using Alcian blue. The average yield was 4–6×10$^6$ cells/animal with mast cells comprising 3–5% of the total cells. Cells were resuspended in Tyrode's solution (see Pearce, F. L. and White, J. R. (1984) *Agents Actions* 14, 392) containing 1 mg/ml bovine serum albumin (Miles Laboratories, Naperville, Ill.). Tyrode's solution was made using distilled, deionized water with 137 mM NaCl, LiCl, or KCl as the major cation species with 1 mM CaCl$_2$ added as indicated.

Cells were prewarmed to 37° C. for 5 minutes and then added in 200 µl aliquots (2–5×10$^3$ mast cells) to polypropylene robes containing an equal volume of buffer with or without copolymer. Total histamine content of the cells was obtained by lysing the cells in 3% perchloric acid. Cells were incubated for 30 minutes at 37° C. and then centrifuged for 5 minutes at 1500×g at 4° C. Supernatants were analyzed for histamine content using the automated fluorometric method (See Siraganian, R. P. (1974) *Anal. Biochem.* 57,383). All samples were performed in duplicate and the results are presented as means of sample pairs. Net percent histamine release was calculated by the following formula:

$$\frac{(\text{Sample release} - \text{Spontaneous Release}) \times 100}{\text{Total Histamine Content}}$$

All of the copolymers shown in Table A were tested for their ability to cause non-cytolytic histamine release. The five copolymers were incubated at a concentration of 100 µg/ml with the mast cells. At the end of 30 minutes incubation with the copolymer, the percent net histamine release was measured. These results are summarized in FIG. 1. As shown, the rates obtained for these copolymers revealed a spectrum of activity with the T130R2 copolymer showing the greatest histamine release and the T150R8 showing the least activity.

Example II - Ionophore Activity

The ionophore activity of the biologically active copolymers was determined by measuring the influx of ions into human red blood cells.

Human blood anticoagulated with lithium heparin was washed 3 times in 0.9% NaCl by centrifugation for 10 minutes at room temperature at 150×g and diluted to 10% hematocrit in saline. For Na$^+$ flux measurements the saline contained approximately 5µ Ci$^{22}$Na$^+$/ml (Amersham Corp., Arlington Heights, Ill.). For determination of Ca$^{++}$ flux, cells were diluted in saline containing 4 mM CaCl$_2$ with $^{45}$Ca$^{++}$ tracer (ICN Biomedicals, Inc., Irvine, Calif.) at approximately 10µ Ci/ml. Cells were warmed to 37° C. in a water bath and then added to equal volumes of prewarmed buffer containing copolymers and mixed by vortexing. For Na$^+$ or Ca$^{++}$ flux measurements, 50 µl duplicate aliquots of each whole suspension were removed during incubation to measure total activity. At selected time points, 200 µl duplicate aliquots were removed and added to 1.5 ml minicentrifuge tubes (American Scientific Products, McGaw Park, Ill.) containing 200 µl SF1154 silicone oil (General Electric Co., Waterford, N.Y.).

For Na$^+$ and Ca$^{++}$ measurements, the supernatants above the oil were aspirated and the portion of the tube above the oil was washed twice by carefully adding and then aspirating distilled water. After removal of most of the oil the cells were resuspended in 250 µl distilled water. Residual $^{22}$Na$^+$ activity was measured using a gamma counter and remaining $^{45}$Ca$^{++}$ activity was measured in a beta counter after mixing 100 µl of the lysate with 3 ml Opti-Fluor LSC cocktail (United Technologies Packard). Determination of potassium efflux was performed as above except that the cells were mixed with copolymer in normal saline at a 10% final hematocrit. After centrifugation, supernatants were removed and assayed for potassium content by flame emission spectroscopy using an IL 443 Flame Photometer (Instrumentation Laboratory, Inc., Lexington, Mass.).

Residual counts in the pellets or the amount of K$^+$ in the supernatants were normalized for pellet hemoglobin content which was determined using Drabkin's solution. There was no difference between hemoglobin content of pellets incubated with any of the copolymers used or with buffer alone indicating that copolymers are not cytolytic. All experiments were performed at least in duplicate.

Five copolymers were tested for their ability to cause influx of Na$^+$ ions over a period of 30 minutes. The results of these tests am summarized in FIG. 2.

Comparison of the rates obtained for these copolymers revealed a spectrum of activity which correlated with their ability to trigger in vitro histamine release from murine mast cells and in vivo inflammation as determined by peak footpad swelling following subplantar injection in mice. These results are summarized in FIG. 3.

The larger the sodium flux observed with each copolymer, the more histamine release and inflammation the copolymer induced.

Example III- Histamine Release vs. Footpad Swelling

Three octablock and seven reverse octablock copolymers were obtained from the BASF Parsipanny, N.J. Resident peritoneal leukocytes were obtained by lavage as described in Example 7.2.

Six of seven reverse octablock copolymers were found to release significant amounts of histamine from mouse peritoneal mast cells. These results are summarized in Table B.

TABLE B

| | \multicolumn{4}{c}{Histamine Release Compared to Footpad Swelling Induced by Copolymers} | | | |
|---|---|---|---|---|---|
| | Avg[a] | Chain[b] | % Histamine Release[c] | | Peak Footpad[d] |
| Copolymer | MW | Structure | 10 µg/ml | 100 µg/ml | Swelling (mm) |
| T130R2 | 7,740 | N-10-26 | 58.0 ± 8.6 | 66.3 ± 6.5 | 2.92 ± 0.41 |
| T130R1 | 6,800 | N-4-26 | 16.3 ± 4.0 | 29.0 ± 7.0 | 1.65 ± 0.3 |
| T110R1 | 5,220 | N-3-21 | 16.7 ± 2.6 | 15.7 ± 2.6 | 1.3 ± 0.3 |
| T90R1 | 4,580 | N-3-18 | 15.7 ± 2.6 | 13.3 ± 2.5 | 1.18 ± 0.24 |
| T150R1 | 8,000 | N-5-32 | 9.0 ± 0.8 | 11.7 ± 3.1 | 1.17 ± 0.08 |
| T150R4 | 11,810 | N-27-32 | 0.3 ± 0.5 | 16.3 ± 7.9 | 1.04 ± 0.5 |
| T150R8 | 20,400 | N-92-32 | 0.7 ± 0.5 | 0.0 ± 0.0 | 0.79 ± 0.01 |

TABLE B-continued

| | | | Histamine Release Compared to Footpad Swelling Induced by Copolymers | | |
|---|---|---|---|---|---|
| | Avg[a] | Chain[b] | % Histamine Release[c] | | Peak Footpad[d] |
| Copolymer | MW | Structure | 10 μg/ml | 100 μg/ml | Swelling (mm) |

[a]Average Molecular Weight (data from manufacturer)
[b]Reverse octablocks are 4-chain structures arranged around a core of ethylenediamine moiety. Chain structure is here represented by the amine nitrogen (N) followed by the average number of POE blocks (underlined) and the number of POP blocks in one chain.
[c]Mean histamine content of supernatants from cells incubated for 30 minutes at 37° C. with copolymers at the indicated concentrations. Mean ± standard deviation for three experiments. Values are corrected for spontaneous release which was always less than 10%.
[d]Rank order of peak footpad swelling produced by subplantar injection of 50 μl of an oil in water emulsion containing 1.25 mg copolymer (mean ± SE on groups of 10 mice.)

The amount of histamine released by the various copolymers was related to the level of inflammation at the site of injection, i.e., the more inflammatory the copolymer in vivo, the more histamine release in vitro.

Example IV - Thymus Stimulation Activity

Six week old female ICR outbred mice were injected in the rear footpads with an oil-in-water emulsion containing copolymer 1.25 mg T150R1, 2.5 mg mineral oil and 25 μg bovine serum albumin in 0.05 ml of 0.01M phosphate buffered saline containing 0.1% Tween 80. Identical injections were made into both rear footpads. Controls were animals that were injected with emulsions without the T150R1. Animals were sacrificed at 4 days 1, 2, 3 and 6 weeks. Their thymuses were carefully dissected free of connective tissue and were weighed.

Microscopic examination revealed that the changes in the thymus were limited almost exclusively to the cortical lymphocytes. Their numbers were markedly reduced three days after injection, but approached normal at one week. After the transient decrease in the number of lymphocytes, the size of the thymus glands of treated animals increased markedly over those of controls. The medullary areas demonstrated little change, but the cortical areas were much larger than normal. The cortical areas of the thymus were composed of immature and mature small lymphoid cells. The reduction in size of the thymus in controls was the expected result of normal involution with aging. Thus, the injection of T150R1 prevented involution during the time studied. In several experiments carried out with identical protocol, the thymuses of treated animals was consistently nearly twice as large as those of the controls. Some treated mice were followed for over eighteen months and appear healthy.

Table C shows that the inhibition of involution of the thymus is long term. The weights of the body, thymus and spleens were after 18 months.

TABLE C

| | Control (n = 3) | injected at 4 weeks (n = 3) | injected at 6 weeks (n = 3) |
|---|---|---|---|
| body | 40.7 ± 7 g | 47.0 ± 4.2 g | 53.3 ± 1.6 g |
| thymus | 34.7 ± 5.0 mg | 67.6 ± 18.7 mg | 66.2 ± 26 mg |
| spleen | 126.7 ± 47.3 mg | 180.7 ± 61.0 mg | 122.7 ± 19 mg |

Histological examination of the thymuses showed little thymus tissue in control mice. Thymuses of injected mice had "young looking" thymus tissue.

Example V - Thymus Stimulation, Copolymer in Saline

Mice were injected via the tail vein with the following preparations:
1. Saline at 4° C.
2. 2.5 mg of copolymer T150R1 in saline at 4° C.
3. 1μ beads coated with T150R1 copolymer.

Each experimental group contained four mice. After 6 days, the mice were sacrificed and the thymuses were carefully dissected and weighed. The results of this experiment are summarized in FIG. 4.

This Example shows that the copolymer dissolved in cold saline and injected directly into the blood of an animal causes a marked increase in the weight of the thymus.

Example VI - Thymus Stimulation, Oil and Water Emulsion

Mice were injected in the footpad with related copolymers and other forms of emulsion. Copolymers T130R2 and T1501 had weaker effects in stimulating the increased size of the thymus. The results of an experiment with water in oil emulsions is shown in Table D.

TABLE D

| | WATER-IN-OIL EMULSIONS Weight of the thymus in mg | |
|---|---|---|
| Copolymer | 2 weeks | 6 weeks |
| T150R1 | 65 ± 7 | 110 ± 7 |
| T1501 | 84 ± 15 | 77 ± 4 |
| Vehicle Control | 101 ± 18 | 50 ± 7 |

Example VII - Thymus Stimulation, General Observations

Mice were treated as in Example 7.6 and carefully observed for a period of several months. The following observations were made. The treated mice were larger than control mice. The treated mice appeared to exhibit increased motor activity including more general activity in the cage, excessive grooming and the treated mice ate more than the control mice.

The uterus of the treated female mice was larger and appeared to have increased vascularity. There was an increased prominence of Peyer's patches (gut associated lymphoid tissue) in the treated animals.

Example VIII - Growth Stimulation, Comparison of Copolymers

The biologically active copolymer of the present invention was administered to mice. The growth of the mice was then measured after six weeks.

Oil-in-water emulsions were prepared with 1 mg bovine serum albumin (BSA), 50 mg of the indicated copolymer (all copolymers were manufactured by BASF Corporation, Parsipanny, N.J.) and 100 μl mineral oil (Drakeol 6VR, Penreco Refining Company, Butler, Pa.) in 2 ml of phosphate-buffered saline (PBS) with 0.2% Tween 80 (Sigma Chemical Co., St. Louis, Mo.). The mixture was homogenized in a Potter Evehjin homogenizer. The oil, copolymer and BSA were homogenized together before adding the phosphate buffered saline. The mixture was then further homogenized to form a fine emulsion.

Emulsions were prepared of each of the copolymers shown in Table D. Each of these copolymers is comprised of blocks of polyoxyethylene (POE) and polyoxypropylene (POP) arranged in the fashion previously described for copolymer T150R1. They differ from one another only in the size of the blocks. Each has characteristic physiochemical and biologic properties.

Mice were injected with 50 μg of BSA, 2.5 mg copolymer and 5 mg oil in 0.1 ml of an oil-in-water emulsion divided between the two hind feet. Their weights six weeks later are summarized in Table E.

TABLE E

| Copolymer | Molecular Wt (Hydrophobe) | Percent Hydrophile[a] | Mean Wt[b] |
|---|---|---|---|
| T90R1 | 3750 | 10% | 22.7 ± 1.03 gm |
| T110R1 | 4750 | 10% | 22.7 ± 0.76 gm |
| T130R1 | 5750 | 10% | 23.3 ± 1.36 gm |
| T130R2 | 5750 | 20% | 24.7 ± 0.62 gm |
| T150R1 | 6750 | 10% | 26.7 ± 1.75 gm |
| T150R4 | 6750 | 40% | 23.5 ± 1.77 gm |
| T150R8 | 6750 | 80% | 23.0 ± 1.06 gm |

[a]Percentages are to the nearest 10%
[b]Mean weight of groups of five mice ± standard deviation The mice injected with the emulsion containing the copolymer T150R1 were visibly larger than those injected with any of the other copolymers. All of the mice appeared healthy.

All of the copolymers used in Table E consist of blocks of polyoxypropylene (POP) and polyoxyethylene (POE) attached in the same reverse octablock configuration. The compounds differ from one another only in the size of the blocks of each compound. These differences, however, confer distinct physiochemical properties on the copolymers which correlate with their biologic activities.

Example IX - Growth Stimulation, Effect of Various Emulsions

Oil-in-water emulsions were prepared using 1 mg bovine serum albumin (BSA), 50 mg of either copolymer T1501 or T150R1 (BASF Corporation, Parsippany, N.J.) and 100 μl mineral oil (Drakeol 6VR, Penreco, Butler, Pa.) in 2.0 ml phosphate buffered saline with 0 2% Tween 80 in a Potter Evehjin homogenizer as described above. The control oil-in-water emulsion was prepared identically except that no copolymer was used.

Copolymer T1501 has the following general structure:

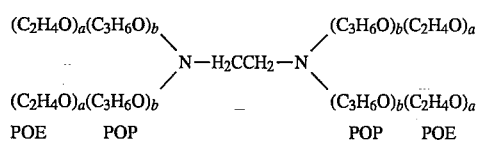

and copolymer T150R1 has the following general structure:

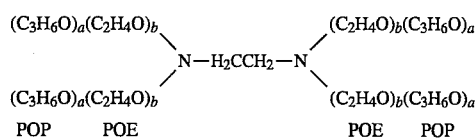

The hydrophobic polyoxypropylene block in each of the structures have a mean aggregate molecular weight of approximately 6750. They each contain approximately 10% hydrophilic polyoxyethylene.

The water-in-oil emulsion was prepared using 50 mg of either copolymer T1501 or T150R1, 1.2 ml Freund's incomplete adjuvant (Sigma Chemical Company, St. Louis, Mo.), and 0.8 ml Hank's balanced salt solution (Gibco, Grand Island, N.Y.), containing 1 mg bovine serum albumin (BSA). The control emulsion was prepared identically except that it contained no copolymer.

Mice were injected with 2.5 mg of copolymer in 0.1 ml of either the oil-in-water or water-in-oil emulsion. Controls consisted of mice injected with the same dose of an identical emulsion which contained no copolymer. The injections were given subcutaneously and the total dose was divided between the two hind feet. Their weights at six weeks are summarized in Table F.

TABLE F

| | MEAN WEIGHT[a] | |
|---|---|---|
| COPOLYMER | Oil-in-water Emulsion | Water-in-Oil Emulsion |
| T1501 | 21.2 ± 1.92 grams | 26.6 ± 1.18 grams |
| T150R1 | 28.1 ± 0.72 grams | 26.5 ± 2.32 grams |
| Control | 22.5 ± 0.96 grams | 23.0 ± 1.41 grams |

The block copolymer designated T150R1 was highly effective in stimulating growth in both water-in-oil emulsion and in oil-in-water emulsion. The block copolymer designated T1501 was effective in stimulating growth in a water-in-oil emulsion.

Example X - Stimulation of Motor Activity

The effect the biologically-active copolymer of the present invention has on the motor activity of rats was measured. The animals used in this Example were adult male Sprague-Dawley rats.

The rats were individually housed in suspended cages. All rats were housed for three weeks in the same room prior to initiation of the study.

Baseline measurements of horizontal locomotor activity were made for one week prior to administration of the copolymer. Horizontal activity was measured using an activity box (Omnitech, Inc., Columbus, Ohio) interfaced with a Vic 20 microcomputer.

The activity box has two rows of 8 photocells positioned at 90° angles. When the light path to a photocell is broken, a voltage drop occurs and is recorded by the computer. Activity determinations were made on all nine rats at three day intervals.

The test and control solutions were prepared as follows: The aqueous phase was prepared by mixing 100 ml of PBS and 0.2 ml of Tween-80. This mixture was stirred approximately 5 minutes. 200 µl of oil (Drakeol, Penreco, Butler, Pa.) was added to 100 µl of T150R1. This mixture of biologically active copolymer and oil was homogenized for two minutes in a Potter Evehjin homogenizer. Next, 1 ml of PBS with 2% Tween-80 was added and homogenized for another 2 minutes. Finally, an additional 1 ml of PBS with 2% Tween 80 was added and homogenized for 2 minutes. The control emulsion was prepared as above but without the addition of T150R1 copolymer.

All rats were injected with 100 µl of either the control or the test emulsion. The test emulsion contained a total of 5 mg of T150R1 copolymer. All injections were given subcutaneously on the dorsum of the neck. The effect of the compound on the activity of rats is shown in FIG. 5.

As shown FIG. 5, rats that were injected with the biologically active copolymer of the present invention demonstrated markedly increased activity over the control.

Example XI - Tumoricidal Activity

The effects of the biologically-active copolymer of the present invention on a human leukemic cell line were evaluated. The biologically-active copolymer (T150R1) tested had the following formula:

$$\begin{matrix} (C_3H_6O)_a(C_2H_4O)_b & & (C_2H_4O)_b(C_3H_6O)_a \\ & \diagdown \quad \diagup & \\ & N-H_2CCH_2-N & \\ & \diagup \quad \diagdown & \\ (C_3H_6O)_a(C_2H_4O)_b & & (C_2H_4O)_b(C_3H_6O)_a \\ \text{POP} \quad \text{POE} & & \text{POE} \quad \text{POP} \end{matrix}$$

wherein:

The mean molecular weight of the hydrophobe portion of the octablock copolymer represented by polyoxypropylene $(C_3H_6O)_b$ (POP) is approximately 6750 daltons;

a is a number such that the hydrophile portion represented by polyoxyethylene $(C_2H_4O)_a$ (POE) constitutes approximately 10% of the compound by weight; and b is a number such that the polyoxypropylene $(C_3H_6O)_b$ (POP) portion of the octablock copolymer constitutes approximately 90% of the compound by weight.

This biologically active copolymer is designated T150R1.

The effects of the biologically active copolymer T150R1 of the present invention on malignant human cells were evaluated by incubating various doses of the copolymer with K562 acute myeloblastic leukemia cells or HL-60 promyelocytic leukemia cells and determining viable cell numbers by the trypan-blue exclusion method and cellular proliferation as measured by incorporation of $^3$H-thymidine into DNA after two days of culture in CEM medium containing 5% fetal calf serum. The results are shown in FIGS. 6 and 7.

FIG. 6 shows that the biologically-active copolymer of the present invention was highly toxic to HL-60 cells, but only minimally affected the viability of K-562 cells. With a dose of biologically-active copolymer of 10 µg per $10^5$ cells, the viability of HL-60 cells decreased to less than 35% that of control cells incubated with medium only. With 30 µg/$10^5$ cells of biologically-active copolymer, over 90% of the cells were killed. In contrast, over 80% of the K-562 cells were alive with the 10 µg close and over 70% of the K-562 cells were alive with the 30 µg dose of biologically-active copolymer.

As shown in FIG. 7, the biologically-active copolymer of the present invention strikingly inhibited DNA synthesis by both HL-60 and K562. The HL-60 was more greatly affected than the K562 cell line. However, with the 30 µg dose at which greater than 70% of the K562 cells in the culture were alive, DNA synthesis by these cells was inhibited greater than 85%.

Thus, the biologically-active copolymer of the present invention showed both cytotoxic and cytostatic effects against two human leukemia cell lines. The fact that HL-60 was much more susceptible than was K562 shows that the copolymer was selective for the HL-60.

Example XII - Differential Effect of Copolymers on Leukemic Cell Lines

FIG. 8 shows the results of differential effect of the biologically active copolymers of the present invention on two different cell lines. In addition to the biologically-active copolymer T150R1 tested in Example 7.11, T130R1 represented by the following formula:

$$\begin{matrix} (C_3H_6O)_a(C_2H_4O)_b & & (C_2H_4O)_b(C_3H_6O)_a \\ & \diagdown \quad \diagup & \\ & N-H_2CCH_2-N & \\ & \diagup \quad \diagdown & \\ (C_3H_6O)_a(C_2H_4O)_b & & (C_2H_4O)_b(C_3H_6O)_a \\ \text{POP} \quad \text{POE} & & \text{POE} \quad \text{POP} \end{matrix}$$

wherein:

The mean molecular weight of the hydrophobe portion of the octablock copolymer represented by polyoxypropylene $(C_3H_6O)_b$ (POP) is approximately 5750 daltons;

a is a number such that the hydrophile portion represented by polyoxyethylene $(C_2H_4O)_a$ (POE) constitutes approximately 10% of the compound by weight; and b is a number such that the polyoxypropylene $(C_3H_6O)_b$ (POP) portion of the octablock copolymer constitutes approximately 90% of the compound by weight.

Cell cultures were incubated with various concentrations of the two copolymers. After 24 hours of incubation, the level of lactic dehydrogenase (LDH) was measured in the supernatant and compared to the total LDH in untreated cells. The release of LDH into the surrounding medium is a measure of cell death. As shown in FIG. 8, the two cell lines responded very differently to the two drugs.

Thus, the tumoricidal compound of the present invention showed both cytotoxic effects against two human leukemia cell lines. HL-60 cell line was more sensitive to the T150R1 while the K-562 was much more sensitive to the T150R2 copolymer.

Example XIII - Differentiation of Leukemic Cell Lines

The effects of low concentrations of octablock copolymer T130R2 were determined on the HL-60 cell lines. T130R2 octablock copolymer causes inhibition of the proliferation and retards DNA synthesis over time. T130R2 causes cell lysis at concentrations greater than 10 µg/ml after a 24 hour incubation. However, at lower concentrations, T130R2 causes a dose dependent increase in cell adherence starting at a concentration of approximately 1 µg/ml to a concentration of approximately 30 µg/ml. After 24 hours of incubation, over 50% of the normally nonadherent HL-60 cells are adherent. The data indicates that the HL-60 cells differentiate when exposed to the T130R2 copolymer. The evidence that supports this observation is as follows: (a) An incubation of at least 2 days was required to arrest growth; (b) T130R2-treatment caused cells to adhere to the bottom of the plate, which is an indication of differentiation into monocytic cells; (c) cell-cycle analysis showed two levels of blockade, namely, G0+G1–S and G2+M–G0–G1 phases of cell-cycle.

Example XIV - Immunosuppressive Activity

In an experiment to investigate the effects of T150R1 on antibody production, groups of four mice were administered the antigen, bovine serum albumin, in an oil-in-water emulsion with or without T150R1. The mice were challenged 14 days later with BSA plus an adjuvant and the antibody response to the antigen was measured at 1, 2, and 3 weeks. As shown in FIG. 9, antibody titers in the T150R1 treated animals were less than 1000:1 at all three time points whereas the control mice displayed increasing titers with an average titer greater than 4000:1 at three weeks following challenge.

Example XV - Adoptive Transfer of Immunosuppression

In another experiment, mice were administered BSA in an oil-in-water emulsion with or without T150R1 as in the above experiment. Mice were sacrificed 14 days later. Thymus and spleen were removed and single cell suspensions of thymus or spleen were administered intravenously to syngenic recipient mice. Mice were challenged at the same time with BSA in an oil-in-water emulsion with adjuvant. Titers to the BSA were measured at 1, 2, and 3 weeks. These results are shown in FIG. 10.

As shown in FIG. 10, mice receiving thymus cells had titers below 1000:1 at all three time points. Those receiving spleen cells had titers below 1000:1 at 1 and 2 weeks and below 3500:1 at 3 weeks. Control mice which did not receive thymus or spleen cells had steadily increasing titers which at three weeks averaged greater than 4000:1. This experiment demonstrates adoptive transfer of immunosuppression with spleen and thymus cells.

Example XVI - Suppression of Experimental Allergic Encephalomyelitis

The effect of T150R1 on the progression of experimental allergic encephalomyelitis (EAE), a well characterized animal model of multiple sclerosis, has been studied. In this animal model EAE is induced by injecting myelin basic protein (MBP), a component of the sheath covering certain nerves, in combination with complete Freund's adjuvant (CFA), a potent adjuvant, into Lewis rats, a strain particularly prone to developing autoimmune disease. Over a two week period following injection, the rats develop an ascending flaccid paralysis and characteristic lesions of the central nervous system. In a study designed to investigate T150S1, rats were injected with MBP-CFA with or without T150S1. Animals receiving MBP-CFA developed signs typical of EAE. The T150R1 rats however, showed no evidence of paralysis. All rats were sacrificed at day 13 following injection, the thymuses were removed and single cell suspensions were made and cells were counted. As shown in FIG. 11, the thymus of T150R1 treated rats contained over 40 times the number of cells as the MBP-CFA only treated rats. As an additional control, the response to hen egg albumin injected with CFA and T150R1 was evaluated. These rats also had a greatly increased number of cells in the thymus.

The proliferative activity of thymus cells from T150R1 treated rats, as measured by triated thymidine uptake, was also markedly increased over the MBP-CFA animals. The in vitro response to challenge with MBP was also evaluated by measuring triated thymidine uptake. In this experiment, T150R1-MBP-CFA treated animals demonstrated higher levels of activity than the MBP-CFA treated animals at 24 hours (See FIG. 12). However, at 72 and 96 hours T150R1 treated animals had negligible thymidine incorporation while the MBP-CFA rats maintained levels of incorporation comparable to the 24 hour value.

Although not wanting to be bound by the following theory, it is believed the increased cellularity in the thymus is due to thymic stimulation with the dominant response being stimulation of specific suppressor cells. The ability to induce a specific suppressor cell response has implications for those diseases or conditions in which a specific tolerant state is desired.

Example XVII - Immunomodulation in Poultry, Bursal Weight

Chickens are treated subcutaneously at one day of age with an oil-in-water emulsion of the copolymer T150R1. A 2.5 mg dose of the copolymer is administered. Relative bursal weights at 1, 3, and 6 weeks of age are determined and the results are set forth in Table G. A comparison is made of chickens treated with the polymer in the oil-in-water emulsion against chickens treated with the oil-in-water vehicle only. No difference in bursal weight is found at 1 week of age. Male and female chickens treated with the polymer have significantly smaller bursae at 3 weeks of age than chickens injected with the vehicle alone. At 6 weeks of age, there is no difference in bursal weights of the treated and untreated female chickens, but the difference in males is more pronounced. In fact, many of the male birds have effete bursae at 6 weeks. It is known in the art that testosterone and its analogues cause bursal atrophy which probably is due to enhanced B cell emigration. The pronounced effect on bursal weights in males in this experiment may be due to an additive effect of testosterone which reaches significant levels around the fourth week of age.

Antibody assays are done with sera collected from the treated chickens by commercial ELISA tests. It can be concluded from these tests that bursal atrophy is not caused by adventitial infection with infectious bursal disease virus as representative serum samples do not have measurable levels of antibodies to it, or to other common viruses of poultry. The observed results therefore are most likely the result of treatment with T150R1.

TABLE G

| Age (wks) | Relative bursal weights[a] | | | | Unsexed Vehicle |
|---|---|---|---|---|---|
| | Females | | Males | | |
| | T150R1 | Vehicle | T150R1 | Vehicle | |
| 1 | — | — | — | — | 0.174  0.173 |
| 3 | 0.314 | 0.292[b] | 0.324 | 0.239[c] | —    — |

TABLE G-continued

Relative bursal weights[a]

| Age (wks) | Females | | Males | | Unsexed Vehicle |
|---|---|---|---|---|---|
| | T150R1 | Vehicle | T150R1 | Vehicle | T150R1 |
| 6 | 0.243 | 0.247 | 0.263 | 0.194[c] | |

[a]Mean relative bursal weights of 125 chickens per group at 1 week, and 225 chickens per group at 3 and 6 weeks
[b]Significantly different from vehicle control, p = 0.0014, pooled t test.
[c]Significantly different from vehicle control, p = 0.0000, pooled t test.

Example XVIII - Immunomodulation in Poultry, Bursal Morphology

Chickens are treated subcutaneously at one day of age with an oil-in-water emulsion of the copolymer T150R1. The doses administered contain 1.0, 2.5 and 5.0 mg of the copolymer.

Morphometric data concerning the bursae of the treated birds are collected by using a SONY® television camera mounted on a light microscope to project images of tissue sections of bursae on a smooth surface. An electronic stylus is used to circumscribe bursal follicles along their outer perimeters and to trace the outer and inner (medullary) margins of the interfollicular epithelium (IFE). The stylus is coupled to an Apple IIe computer which employs a program to convert the electronic signals to square inches of area inscribed. A metric grid is projected and measured with the stylus in order to convert square inches to $\mu m^2$. The cortical area is defined as the difference between follicular area and the area inscribed by the outer margin of the interfollicular epithelium. The area of the interfollicular epithelium is defined as the difference between the medullary area and the area inscribed by the outer margin of the interfollicular epithelium. Twenty-five contiguous lymphoid follicles are measured in each bursa and the coefficient of variance (CV) of these measurements range from 10–35%. Each group analyzed has 20 chickens. The CV for the 20 observations ranges from 5–15%. The data collected at three days, one week, two weeks, and three weeks after treatment are presented in Tables H–K.

At three days of age, the medullae of chicks treated with 1.0 and 2.5 mg T150R1 are larger than medullae of the controls. This enlargement is also reflected in the cortico-medullary (C/M) ratios. Although the medullae tend to be smaller and the cortices larger in treated birds than in controls at 1 week of age, these trends are not statistically significant until they are Considered together in the cortico-medullary ratios. Because the follicles of chickens treated with 1.0 mg T150T1 are unusually small at two weeks (as shown in Table J), a direct comparison with the other dosage groups is risky. Nevertheless, at two weeks the cortico-medullary ratio is higher than controls and not different from birds treated with 2.5 mg of the copolymer. At three weeks, the cortico-medullary ratio of birds treated with 2.5 mg T150R1 are greater than controls, but the difference is not as great and the previous perturbation in bursal development probably is subsiding. Although a few differences are observed in areas of the interfollicular epithelium, no pattern can bed discerned and these differences are considered inconsequential. As shown in Tables I, J, and K, the 5.0 mg does appears to be less effective than the 2.5 mg dose. Apparently a dose containing 1.0 mg or 2.5 mg of the copolymer T150R1 accelerates the maturation of the bursa of Fabricius.

Accordingly, precocious maturation of bursae should lead to more rapid growth of medullae which should begin to regress early. Early migration of medullary cells to the cortices should results in more rapid expansion of cortices than normal. As the cortical lymphocytes mature and migrate to the spleen, bursal involution should occur at an earlier age, and be evident in males earlier than females. These are the changes observed.

TABLE H

Morphometry of Lymphoid Follicles Three Days After Treatment[1,2]

| Treatment | Follicle | Medulla | IFE | Cortex | C/M |
|---|---|---|---|---|---|
| None | 28,900 | 3,340[a] | 7,280[a] | 18,300 | 5.6[a] |
| Vehicle | 28,800 | 3,340[a] | 8,360[a,b] | 17,000 | 5.0[a,c] |
| 1.0 mg | 33,400 | 6,050[b] | 9,670[b] | 17,700 | 2.9[b] |
| 2.5 mg | 31,800 | 4,580[c] | 9,130[a,b] | 18,000 | 4.1[c] |
| 5.0 mg | 26,400 | 3,000[a] | 7,460[a,b] | 16,000 | 5.4[a] |

[1]Values are mean areas of 25 contiguous follicles, their medullae, cortices and zones of interfollicular epithelium (IFE) in $\mu m^2$, and their mean cortimedullary ratios (C/M) from 20 chickens.
[2]Means which do not share a superscript differ significantly at $p \leq 0.05$ by analysis of variance, using the Tukey test to identify significant differences.

TABLE I

Morphometry of Lymphoid Follicles One Week After Treatment[1,2]

| Treatment | Follicle | Medulla | IFE | Cortex | C/M |
|---|---|---|---|---|---|
| None | 64,600 | 11,900 | 21,000[a] | 31,700 | 2.7[a] |
| Vehicle | 53,800 | 8,870 | 16,000[a,b] | 28,400 | 3.3[a,d] |
| 1.0 mg | 56,800 | 7,190 | 14,300[b] | 35,400 | 5.4[b] |
| 2.5 mg | 54,500 | 7,200 | 14,500[b] | 32,900 | 4.8[b,c] |
| 5.0 mg | 62,500 | 9,650 | 16,900[a,b] | 35,900 | 3.8[c,d] |

[1]Values are mean areas of 25 contiguous follicles, their medullae, cortices and zones of interfollicular epithelium (IFE) in $\mu m^2$, and their mean cortimedullary ratios (C/M) from 20 chickens.
[2]Means which do not share a superscript differ significantly at $p \leq 0.05$ by analysis of variance, using the Tukey test to identify significant differences.

TABLE J

Morphometry of Lymphoid Follicles Two Weeks After Treatment 1,2

| Treatment | Follicle | Medulla | IFE | Cortex | C/M |
|---|---|---|---|---|---|
| None | 228,000[a,c] | 42,600[a] | 65,200[a] | 120,000 | 2.9[a] |
| Vehicle | 213,000[a,c] | 39,800[a] | 57,400[a] | 116,000 | 3.1[a] |
| 1.0 mg | 170,000[a] | 19,300[b,c] | 43,700[b] | 107,000 | 5.4[b] |
| 2.5 mg | 274,000[b,c] | 35,900[a,c] | 65,400[a] | 173,000 | 5.0[b] |
| 5.0 mg | 242,000[a,c] | 43,600[a] | 65,400[a] | 133,000 | 3.3[a] |

[1]Values are mean areas of 25 contiguous follicles, their medullae, cortices and zones of interfollicular epithelium (IFE) in $\mu m^2$, and their mean cortimedullary ratios (C/M) from 20 chickens.

TABLE J-continued

Morphometry of Lymphoid Follicles Two Weeks After Treatment 1,2

| Treatment | Follicle | Medulla | IFE | Cortex | C/M |
|---|---|---|---|---|---|

[2]Means which do not share a superscript differ significantly at $p \leq 0.05$ by anaylsis of variance, using the Tukey test to identify significant differences.

TABLE K

Morphometry of Lymphoid Follicles Three Weeks After Treatment[1,2]

| Treatment | Follicle | Medulla | IFE | Cortex | C/M |
|---|---|---|---|---|---|
| None | 436,000 | 72,900 | 102,000 | 256,000 | 3.7[a] |
| Vehicle | 429,000 | 74,500 | 118,000 | 236,000 | 3.3[a] |
| 1.0 mg | 500,000 | 76,600 | 129,000 | 295,000 | 4.0[a] |
| 2.5 mg | 527,000 | 75,500 | 134,000 | 302,000 | 4.2[b] |
| 5.0 mg | 478,000 | 74,800 | 132,000 | 272,000 | 3.8[a,b] |

[1]Values are mean areas of 25 contiguous follicles, their medullae, cortices and zones of interfollicular epithelium (IFE) in $\mu m^2$, and their mean cortimedullary ratios (C/M) from 20 chickens.
[2]Means which do not share a superscript differ significantly at $p \leq 0.05$ by analysis of variance, using the Tukey test to identify significant differences.

Example XIX - Immunostimulation in Poultry

Chickens treated with 1.0 mg of the copolymer T150R1 in an oil-in-water emulsion at one day of age are immunized at one and two weeks with sheep red blood cells (SRBC) and killed *Brucella abortus* (BA) to elicit primary and secondary antibody responses, as described by the method of Bhanushali et al., (See Bhanushali, J. K., K. K. Murthy and W. L. Ragland, The effects of in ovo mibolerone treatment on the bursa of Fabricius and the humoral immune system of chickens: A dose-response study. *Immunopharmacology* 10:99–110, 1985) which is incorporated by reference herein. Results of an experiment with 20 chickens per group are shown in Table L. Most of the birds demonstrate no measurable primary response to either antigen. The total Ig response, but not the IgG secondary response, to sheep red blood cells is significantly higher in chickens which have been treated with a dose containing 1.0 mg T150R1 than in the other three groups. Secondary responses to *Brucella abortus* in treated birds are not different from birds injected with the vehicle alone.

In a subsequent immunization experiment, 40 chickens are treated with 1.0 mg T150R1 and 40 with the vehicle. The data am shown in Table M. The total secondary Ig responses to both *Brucella abortus* and sheep red blood cells are significantly increased but there is no significant effect on class switching to IgG, i.e., the effect is only on IgM.

TABLE L

Antibody Responses to Sheep Red Blood Cells (SRBC) and Killed *Brucella abortus* (BA) for 20 chickens

| | SRBC Titers[a] | | | BA Titers[a] | | |
|---|---|---|---|---|---|---|
| | | Secondary | | | Secondary | |
| Treatment | Primary | −2 ME | +2 ME | Primary | −2 ME | +2 ME |
| Vehicle | 0.21 | 4.42 | 0.53 | 0.89 | 4.95 | 0.74 |
| 1.0 mg | 0.22 | 6.00[b] | 2.22 | 0.83 | 5.11[b] | 0.83 |
| 2.5 mg | 0.72 | 5.47 | 2.00 | 1.17 | 4.72 | 0.94 |
| 5.0 mg | 0.12 | 5.59 | 1.76 | 0.89 | 4.95 | 0.74 |

[a]Total immunoglobulin titers are measured with untreated serum (−2 ME) and IgG titers with serum to which 2-mercaptothanol has been added (+2 ME). Titer is determined by $\log_2$ of the reciprocal of the highest serum dilution to cause agglutination.
[b]Significantly different from vehicle control, $p \leq 0.05$.

TABLE M

Antibody Responses to Sheep Red Blood Cells (SRBC) and Killed *Brucella abortus* (BA) for 40 chickens

| | SRBC Titers[a] | | | BA Titers[a] | | |
|---|---|---|---|---|---|---|
| | | Secondary | | | Secondary | |
| Treatment | Primary | −2 ME | +2 ME | Primary | −2 ME | +2 ME |
| Vehicle | 0.69 | 4.46 | 0.66 | 0.45 | 5.45 | 0.90 |
| 1.0 mg | 0.97 | 5.20[b] | 0.69 | 0.84 | 6.23[b] | 0.83 |

[a]Total immunoglobulin titers are measured with untreated serum (−2 ME) and IgG titers with serum to which 2-mercaplvethanol has been added (+2 ME). Titer is determined by $\log^2$ of the reciprocal of the highest serum dilution to cause agglutination.
[b]Significantly different from vehicle control, $p \leq 0.05$.

In the first above-described experiment involving immunized chickens, heparinized blood is collected and buffy coats are prepared for blastogenic tests. Proliferation of lymphocytes stimulated with phytahemagglutinin and concanavalin A are not different from vehicle controls suggesting that the polymer has little effect in cell-mediated responses in chickens. Data are not shown.

It should be understood, of course, that the foregoing relates only to a preferred embodiment of the present invention and that numerous modifications or alterations may be made therein without departing from the spirit and the scope of the invention as set forth in the appended claims.

Example XX - Reduction of the Number of Enteric Microorganisms in the Gut of Animals Biologically active polymers of the present invention are administered to animals to reduce the number of enteric microorganisms in the gut of the animal. Preferred copolymers for reducing enteric microorganisms include T110R1, T130R2 and T150R1, described above in Table A. The preferred animal to treat with the biologically active copolymers of the present invention are poultry animals for the reduction of Salmonella.

A protocol for evaluation of effect of copolymer T150R1 on Salmonella of broiler chickens is described below.

Feed:

Standard unmedicated broiler starter ration supplied by the University of Georgia feed mill (UGA Broiler Starter), described in Table O, was used. Feed contained either zero or 10 ppm T150R1. The premix of copolymer supplied by CytRx was mixed for 15 minutes in a commercial type cement mixer. Chicks were given the appropriate feed ad libitum.

UGA BROILER STARTER
(With Dicalcium Phosphate)
(To be used from 0 to 3–4 weeks of age)

| Ingredient | % | lb/ton |
|---|---|---|
| Ground corn | 55.93 | 1119 |
| Soybean meal, dehulled | 33.71 | 674 |
| Poultry fat | 3.64 | 73 |
| Poultry by-product meal | 3.00 | 60 |
| Dicalcium phosphate | 1.54 | 30.8 |
| Limestone | 1.23 | 24.6 |
| Salt | 0.41 | 8.3 |
| Vitamin mix[1] | 0.25 | 5.0 |
| D,L Methionine (98%) | 0.19 | 3.7 |
| UGA Trace mineral mix[2] | 0.05 | 1.0 |
| Selenium premix[3] | 0.05 | 1.0 |

| Calculated composition | |
|---|---|
| Metabolizable energy, kcal/kg | 3100 |
| Protein, % | 23.0 |
| Ca, % | 1.0 |
| P, total % | 0.73 |
| Available P, % | 0.48 |
| Methionine + cystine, % | 0.93 |
| Lysine, % | 1.26 |
| Na, % | 0.2 |

[1]Vitamin premix provides (per kg/diet): vitamin A, 5,500 IU; vit. $D_8$, 1100 ICU; vitamin E, 11 IU; riboflaven, 4.4 mg; Ca pantothenate, 12 mg; nicotinic acid, 44 mg; choline Cl, 220 mg; vitamin $B_{12}$, 6.6 mg; vitamin $B_6$, 2.2 mg; menadione, 1.1 mg (as MSBC); folic acid, 0.55 mg; d-biotin, 0.11 mg; thiamine, 2.2 mg (as thiamine mononitrate); ethoxyquin, 125 mg.
[2]Trace mineral mix provides (ppm of diet); Mn, 60; Zn, 50; Fe, 30; Cu, 5; I, 1.5.

TABLE N

Corn Meal Premix with T150R1
Premix is made up in 4-lb. batches

| Premix Conc. ppt | Feed Conc. 1 lb. premix/T feed ppm | Corn Oil 4% g/lb. | CLR87-61 g/lb. | Corn Meal g/lb. | Total g/lb. |
|---|---|---|---|---|---|
| 0 | 0 | 72.57/0.1600 | 0/0 | 1741.8/3.8400 | 1814.4/4.0000 |
| 2 | 1 | 72.57/0.1600 | 3.63/0.0080 | 1738.2/3.8320 | 1814.4/4.0000 |
| 6 | 3 | 72.57/0.1600 | 10.89/0.0240 | 1730.9/3.8240 | 1814.4/4.0000 |
| 10 | 5 | 72.57/0.1600 | 18.14/0.0400 | 1723.7/3.8000 | 1814.4/4.0000 |
| 20 | 10 | 72.57/0.1600 | 36.29/0.0800 | 1705.5/3.7600 | 1814.4/4.0000 |
| 30 | 15 | 72.57/0.1600 | 54.43/0.1200 | 1687.4/3.7200 | 1814.4/4.0000 |

Mix one pound premix per one ton of feed

Salmonella:

A λ nalidixic acid resistant strain of *S. typhimurium* previously isolated from chickens was inoculated onto a slant of BG sulfa agar with 200 ppm added nalidixic acid and incubated for 24 hours. The slant was then washed with sterile saline and the resulting suspension used to generate a stock culture that was compared to a standard optical density curve to determine the concentration of Salmonella. 0.5 ml of the appropriate dilution of Salmonella was then gavaged into the crop of a chick on the indicated day.

Sampling:

On the indicated kill day, chicks were killed by cervical disarticulation and the ceca aseptically removed and sampled for Salmonellae according to the standard protocol as follows.

RUSSELL RESEARCH CENTER SALMONELLA METHOD

1. Preenrich initial sample (25 gram feed; chick ceca; chicken carcass rinse) in buffered peptone (BP) water (nine times the sample weight) and incubate for 24 hours at 35°–37° C.

2. Transfer 0.1 mL of BP into 9.9 mL tube or TT broth (Difco, Detroit, Mich.) and incubate for 24 hours at 42° C.

3. From the TT, streak for isolation onto BG Sulfa and Modified Lysine Iron Agar (MLIA) plates and incubate for 24 hours at 35°–37° C.

4. Pick suspect Salmonella colonies from plates onto lysine from agar slants and incubate 24 hours at 35°–37° C.

5. Confirm Salmonella with flagellar (H) serology.

Experiments comparing the effects on Salmonella of the copolymer mixed in chicken were conducted according to the following protocol of inoculation and incubation.

| NUMBER OF BIRDS | COPOLYMER ppm | SALMONELLA INOCULUM | KILL DAYS |
|---|---|---|---|
| 12 | 10 | 0 | 14, 21 |
| 12 | 10 | $10^4$/day 3 | 14, 21 |
| 12 | 10 | $10^6$/day 3 | 14, 21 |
| 12 | 10 | $10^8$/day 3 | 14, 21 |
| 12 | 0 | 0 | 14, 21 |
| 12 | 0 | $10^4$/day 3 | 14, 21 |
| 12 | 0 | $10^6$/day 3 | 14, 21 |
| 12 | 0 | $10^8$/day 3 | 14, 21 |
| 24 | 10 | $10^6$/day 1 | 7, 14, 21, 28 |
| 24 | 0 | $10^6$/day 1 | 7, 14, 21, 28 |

The results of these experiments are presented in Tables 1–3.

Table Number 1

| SALMONELLA INOCULUM & INOCULATION DAY | AGE (D) | COPOLYMER FEED AV. CF | CONTROL FEED AV CF |
|---|---|---|---|
| $10^6$ DAY 1 | 7 | 5.5 | 6.2 |
| NONE | 14 | 0.0 | 0.0 |
| $10^4$ DAY 3 | 14 | 1.45 | 2.56 |
| $10^6$ DAY 3 | 14 | 0.5 | 2.77 |
| $10^6$ DAY 3 | 14 | 3.55 | 2.57 |
| $10^6$ DAY 1 | 14 | 4.2 | 4.7 |
| NONE | 21 | 0.0 | 0.0 |
| $10^4$ DAY 3 | 21 | N/A | 2.55 |
| $10^6$ DAY 3 | 21 | 1.25 | 2.55 |
| $10^8$ DAY 3 | 21 | 3.25 | 3.33 |

Table Number 2

| SALMONELLA INOCULUM & INOCULATION DAY | AGE (D) | COPOLYMER FEED AV. CF | CONTROL FEED AV CF |
|---|---|---|---|
| $10^6$ DAY 1 | 7 | 5.12 | 4.87 |
| NONE | 14 | 0.00 | 0.00 |
| $10^4$ DAY 3 | 14 | 0.00 | 0.25 |
| $10^6$ DAY 3 | 14 | 2.18 | 0.74 |
| $10^9$ DAY 3 | 14 | 1.60 | 1.73 |
| $10^6$ DAY 1 | 14 | 1.68 | 1.20 |
| NONE | 21 | 0.0 | 0.00 |
| $10^4$ DAY 3 | 21 | 1.14 | 0.00 |
| $10^6$ DAY 3 | 21 | 1.20 | 0.74 |
| $10^8$ DAY 3 | 21 | 0.45 | 2.68 |
| $10^6$ DAY 1 | 21 | 1.58 | 0.87 |
| $10^6$ DAY 1 | 28 | 1.04 | 0.45 |

Table Number 3

| SALMONELLA INOCULUM & INOCULATION DAY | AGE (D) | COPOLYMER FEED AV. CF | CONTROL FEED AV CF |
|---|---|---|---|
| NONE | 14 | 0.00 | 0.00 |
| $10^4$ DAY 3 | 14 | 0.50 | 0.00 |
| $10^6$ DAY 3 | 14 | 0.70 | 1.32 |
| $10^8$ DAY 3 | 14 | 1.07 | 3.25 |
| NONE | 21 | 0.00 | 0.00 |
| $10^4$ DAY 3 | 21 | 0.00 | 0.00 |
| $10^6$ DAY 3 | 21 | 2.18 | 1.30 |
| $10^8$ DAY 3 | 21 | 2.32 | 1.32 |

It should be understood, of course, that the foregoing relates only to a preferred embodiment of the present invention and that numerous modifications or alterations may be made therein without departing from the spirit and the scope of the invention as set forth in the appended claims.

What is claimed is:

1. A method for reducing microorganisms in the gut of an animal comprising, orally administering to an animal an effective amount of a biologically active copolymer sufficient to reduce the number of microorganisms in the gut of the animal, said biologically active copolymer comprising an octablock copolymer having the following formula:

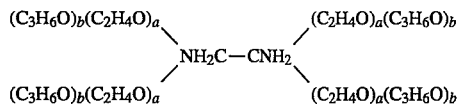

wherein:

the mean aggregate molecular weight of the portion of the octablock copolymer represented by polyoxypropylene is between approximately 5000 and 7000 Daltons;

a is a number such that the portion represented by polyoxyethylene constitutes between approximately 10% to 40% of the compound by weight; and b is a number such that the polyoxypropylene portion of the total molecular weight of the octablock copolymer constitutes between approximately 60% and 90% of the compound by weight.

2. The method of claim 1 wherein said octablock copolymer comprises a compound having the following formula:

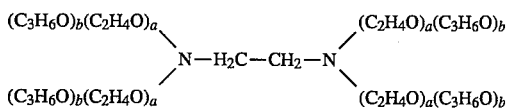

wherein:

the mean aggregate molecular weight of the portion of the octablock copolymer represented by polyoxypropylene is approximately 6750 Daltons;

a is a number such that the portion represented by polyoxyethylene constitutes approximately 10% of the compound by weight; and b is a number such that the polyoxypropylene portion of the total molecular weight of the octablock copolymer constitutes approximately 90% of the compound by weight.

3. The method of claim 1 wherein said octablock copolymer comprises a compound having the following formula:

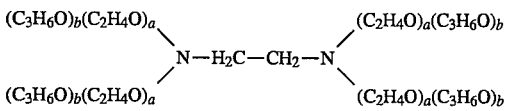

wherein:

the mean aggregate molecular weight of the portion of the octablock copolymer represented by polyoxypropylene is approximately 5750 Daltons;

a is a number such that the portion represented by polyoxyethylene constitutes approximately 10% of the compound by weight; and b is a number such that the polyoxypropylene portion of the total molecular weight of the octablock copolymer constitutes approximately 90% of the compound by weight.

4. The method of claim 1 wherein said octablock copolymer comprises a compound having the following formula:

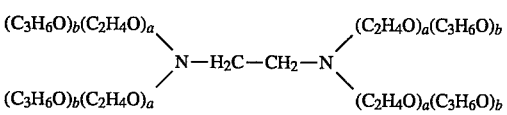

wherein:

the mean aggregate molecular weight of the portion of the octablock copolymer represented by polyoxypropylene is approximately 5220 Daltons;

a is a number such that the portion represented by polyoxyethylene constitutes approximately 10% of the compound by weight; and b is a number such that the polyoxypropylene portion of the total molecular weight of the octablock copolymer constitutes approximately 90% of the compound by weight.

5. The method of claim 1, wherein the animal is a poultry animal.

6. The method of claim 5, wherein the poultry animal is selected from the group consisting of chickens, turkeys, pheasant, quail, geese, and duck.

7. The method of claim 1, wherein the animal is a chicken.

8. The method of claim 1, wherein the animal is a turkey.

9. The method of claim 1, wherein the microorganism is selected from the group consisting of Salmonella., Escherichia, Klebsiella, Enterobacter, Pseudomonas, Serratia, Shigella, Campylobacter, Proteus, Edwardsiella, Yersinia, Eimeria and Vibrio.

10. The method of claim 1, wherein the microorganism is Salmonella.

11. A method for reducing microorganisms in the gut of an animal comprising, orally administering to an animal an effective amount of a biologically active copolymer sufficient to reduce the number of microorganisms in the gut of the animal, said biologically-active copolymer comprising an octablock copolymer having the following formula:

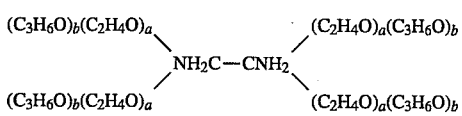

wherein:

the mean aggregate molecular weight of the portion of the octablock copolymer represented by polyoxypropylene is between approximately 5000 and 7000 Daltons;

a is a number such that the portion represented by polyoxyethylene constitutes between approximately 5% to 20% of the compound by weight; and b is a number such that the polyoxypropylene portion of the total molecular weight of the octablock copolymer constitutes between approximately 80% and 95% of the compound by weight.

12. The method of claim 11 wherein said octablock copolymer comprises a compound having the following formula:

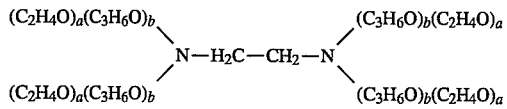

wherein:

the mean aggregate molecular weight of the portion of the octablock copolymer represented by polyoxypropylene is approximately 6750 Daltons;

a is a number such that the portion represented by polyoxyethylene constitutes approximately 10% of the compound by weight; and b is a number such that the polyoxypropylene portion of the total molecular weight of the octablock copolymer constitutes approximately 90% of the compound by weight.

13. The method of claim 11, wherein the animal is a poultry animal.

14. The method of claim 13, wherein the poultry animal is selected from the group consisting of chickens, turkeys, pheasant, quail, geese, and duck.

15. The method of claim 11, wherein the animal is a chicken.

16. The method of claim 11, wherein the animal is a turkey.

17. The method of claim 11, wherein the microorganism is selected from the group consisting of Salmonella, Escherichia, Klebsiella, Enterobacter, Pseudomonas, Serratia, Shigella, Campylobacter, Proteus, Edwardsiella, Yersinia, Eimeria and Vibrio.

18. The method of claim 11, wherein the microorganism is Salmonella.

19. A method for reducing microorganisms in the gut of an animal comprising, orally administering to an animal an effective amount of a biologically active copolymer sufficient to reduce the number of microorganisms in the gut of the animal, said biologically active copolymer comprising an octablock copolymer having the following formula:

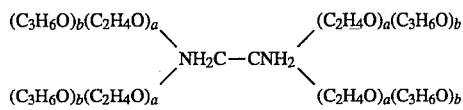

wherein:

the mean aggregate molecular weight of the portion of the octablock copolymer represented by polyoxypropylene is between approximately 5000 and 7000 Daltons;

$a$ is a number such that the portion represented by polyoxyethylene constitutes between approximately 5% to 20% of the compound by weight; and $b$ is a number such that the polyoxypropylene portion of the total molecular weight of the octablock copolymer constitutes between approximately 80% and 95% of the compound by weight.

20. The method of claim 19, wherein the animal is a poultry animal.

21. The method of claim 20, wherein the poultry animal is selected from the group consisting of chickens, turkeys, pheasant, quail, geese, and duck.

22. The method of claim 19, wherein the animal is a chicken.

23. The method of claim 19, wherein the animal is a turkey.

24. The method of claim 19, wherein the microorganism is selected from the group consisting of Salmonella., Escherichia, Klebsiella, Enterobacter, Pseudomonas, Serratia, Shigella, Campylobacter, Proteus, Edwardsiella, Yersinia, Eimeria and Vibrio.

25. The method of claim 24, wherein the microorganism is Salmonella.

* * * * *